(12) United States Patent
Bassler et al.

(10) Patent No.: US 9,752,175 B2
(45) Date of Patent: Sep. 5, 2017

(54) SYSTEMS AND METHODS TO DETECT BIOFILM STREAMER GROWTH AND THEIR USES

(71) Applicant: The Trustees of Princeton University, Princeton, NJ (US)

(72) Inventors: Bonnie L. Bassler, Princeton, NJ (US); Howard A. Stone, Princeton, NJ (US); Knut Drescher, Princeton, NJ (US); Yi Shen, Zurich (CH)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 14/589,845

(22) Filed: Jan. 5, 2015

(65) Prior Publication Data

US 2015/0191765 A1    Jul. 9, 2015

Related U.S. Application Data

(60) Provisional application No. 61/923,806, filed on Jan. 6, 2014.

(51) Int. Cl.
| | |
|---|---|
| C12M 1/34 | (2006.01) |
| C12Q 1/02 | (2006.01) |
| C12Q 1/18 | (2006.01) |

(52) U.S. Cl.
CPC .............. *C12Q 1/18* (2013.01); *C12M 41/36* (2013.01); *C12Q 1/02* (2013.01)

(58) Field of Classification Search
CPC .... A01N 59/00; A01N 2300/00; A01N 35/02; A01N 59/02; A01N 25/30; A01N 57/34; A01N 43/08; A01N 25/34; A01N 63/02; A01N 63/00; B09C 1/002; B09C 1/10; B09C 1/08; C02F 2103/06; C02F 1/78; C02F 1/50; B01L 2200/0673; B01L 2300/0861; B01L 2300/0877; B01L 2400/0487; B01L 2400/0688; B01L 2400/0694; B01L 3/502746; B01L 3/502784; F17D 1/12; G01N 5/0272; G01N 15/1481; G01N 1/28; G01N 2015/0092

See application file for complete search history.

(56) References Cited

U.S. PATENT DOCUMENTS

| | | |
|---|---|---|
| 2014/0246098 A1 | 9/2014 | Fraden et al. |
| 2014/0268321 A1 | 9/2014 | Damiano, Jr. et al. |
| 2014/0273194 A1 | 9/2014 | Handique et al. |
| 2014/0274739 A1 | 9/2014 | Rinker et al. |
| 2014/0306371 A1 | 10/2014 | Guenther et al. |
| 2014/0326339 A1 | 11/2014 | Toner et al. |
| 2014/0335496 A1 | 11/2014 | Grego et al. |

OTHER PUBLICATIONS

Busscher et al., "Microbial Adhesion in Flow Displacement Systems", Clinical Microbiology Reviews, Jan. 2006, p. 127-141, vol. 19, No. 1, Groningen, The Netherlands.
Drescher et al., "Fluid dynamics and noise in bacterial cell—cell and cell—surface scattering", PNAS, Jul. 5, 2011, vol. 108, No. 27, pp. 10940-10945, Tucson, AZ.
Drescher et al., "Biofilm streamers cause catastrophic disruption of flow with consequences for environmental and medical systems", Mar. 12, 2013, vol. 110, No. 11, pp. 4345-4350, Chevy Chase, MD.
Elvers et al., "Binary culture biofilm formation by Stenotrophomonas maltophilia and Fusarium oxysporum", Journal of Industrial Microbiology & Biotechnology, 2001, vol. 26, pp. 178-183, Middlesex, UK.
Escudie et al., "Control of start-up and operation of anaerobic biofilm reactors: an overview of 15 years of research", http://www.ncbi.nlm.nih.gov/pubmed/20713296, Water Res. Jan. 2011;45(1):1-10. doi: 10.1016/j.watres.2010.07.081. Epub Aug. 5. 2010, 2010 Elsevier Ltd., Abstract.
Guaglianone et al., "Microbial biofilms associated with biliary stent clogging", FEMS Immunol Med Microbiol, vol. 59, 2010, pp. 410-420, Ancona, Italy.
Kim et al., "Filaments in curved streamlines: rapid formation of *Staphylococcus aureus* biofilm streamers", New Journal of Physics, vol. 16, 2014, 065024, 19 pages.
Kumar et al., "Significance of microbial biofilms in food industry: a review", Elsevier, International Journal of Food Microbiology, vol. 42, 1998, pp. 9-27, Kamal, India.
Leis et al., "Optically Transparent Porous Medium for Nondestructive Studies of Microbial Biofilm Architecture and Transport Dynamics", Applied and Environmental Microbiology, Aug. 2005, pp. 4801-4808, Duisburg, Germany.
Li et al., "Single-species microbial biofilm screening for industrial applications", Appl Microbiol Biotechnol, 2007, vol. 76, pp. 1255-1262, Biotechnological Products and Process Engineering, Sydney, Australia.
Ludensky, "An automated system for biocide testing on biofilms*", Journal of Industrial Microbiology & Biotechnology, 1998, vol. 20, pp. 109-115, Annandale, NJ.
Marty et al, "Formation of bacterial streamers during filtration in microfluidic systems", Journal Biofouling, vol. 28, 2012, Issue 6, pp. 551-562, Abstract.
Palmer et al., "Bacterial cell attachment, the beginning of a biofilm", J Ind Microbiol Biotechnol, 2007, vol. 34, pp. 577-588, Palmerston North, New Zealand.
Poulsen, "Microbial Biofilm in Food Processing", Lebensm.-Wiss. u.-Technol., vol. 32, pp. 321-326, 1999, Lyngby, Denmark.

(Continued)

*Primary Examiner* — Debbie K Ware
(74) *Attorney, Agent, or Firm* — Michele M. Wales; Inhouse Patent Councel, LLC

(57) ABSTRACT

Methods and systems of measuring biofilms and/or biofilm streamers are presented. The system has at least one channel, a biofilm streamer promotion element, a fluid capable of moving along the channel, wherein the fluid has a flow driven by a controlled pressure; and a measuring element capable of measuring a flow rate of the fluid through the channel. Additionally, methods of screening for compound (s) that promote and/or inhibit biofilm and/or biofilm streamers using this system are also presented. Uses of the system, methods and identified compounds are presented for medical and/or industrial environments.

34 Claims, 13 Drawing Sheets

(56) References Cited

OTHER PUBLICATIONS

Rusconi et al., "Laminar flow around corners triggers the formation on biofilm streamers", Journal of the Royal Society Interface, 2010, vol. 7, pp. 1293-1299, Cambridge, MA.

Rusconi et al, "Secondary Flow as a Mechanism for the Formation of Biofilm Streamers", Biophysical Journal, vol. 100, Mar. 2011, pp. 1392-1399, Princeton, New Jersey.

Shi et al., "Biofilm formation and food safety in food industries", Elsevier, Trends in Food Science & Technology, vol. 20, 2009, pp. 407-413, Shanghai, China.

Hall-Stoodley, "Towards diagnostic guidelines for biofilm-associated infections", Minireview, FEMS Immunol Med Microbial, vol. 65, 2012, pp. 127-145.

Sternberg et al., "Growing and analyzing biofilms in flow cells." Curr Protoc Microbiol. (2006) Chapter 1:Unit 1B.2. doi: 10.1002/9780471729259.mc01b02s00. PubMed—NCBI http://www.ncbi.nlm.nih.gov/pubmed/18770573, Abstract.

Stoodley et al., "Biofilm material properties as related to shear-induced deformation and detachment phenomena", Journal of Industrial Microbiology & Biotechnology (2002), vol. 29, pp. 361-367, Bozeman, MT.

Stoodley et al.,"Flowing biofilms as a transport mechanism for biomass through porous media under laminar and turbulent conditions in a laboratory reactor system.", Biofouling (2005);21(3-4):161-8. PubMed, http://www.ncbi.nlm.nih.gov/pubmed/16371336, Abstract.

Tang et al., "Biofilm growth of individual and dual strains of *Klebsiella oxytoca* from the dairy industry on ultrafiltration membranes", J Ind Microbiol Biotechnol, 2009, vol. 36, pp. 1491-1497, Auckland, New Zealand.

Unger et al., "Monolithic Microfabricated Valves and Pumps by Multilayer Soft Lithography", www.sciencemag.org, Science, vol. 288, Apr. 7, 2000, Pasadena, CA.

Hyde et al., "Comparison of fluorinated polymers against stainless steel, glass and polypropylene in microbial biofilm adherence and removal", Journal of Industrial Microbiology & Biotechnology, 1997, vol. 19, pp. 142-149, Chaska, MN.

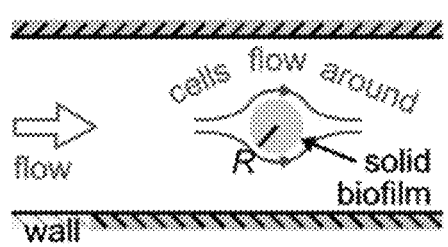
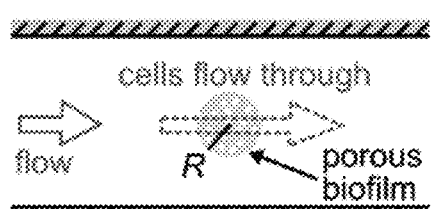
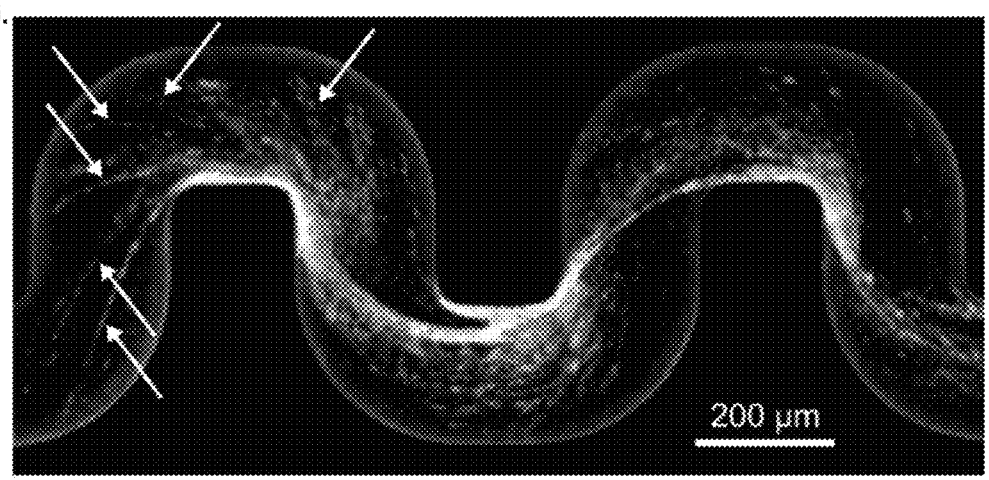
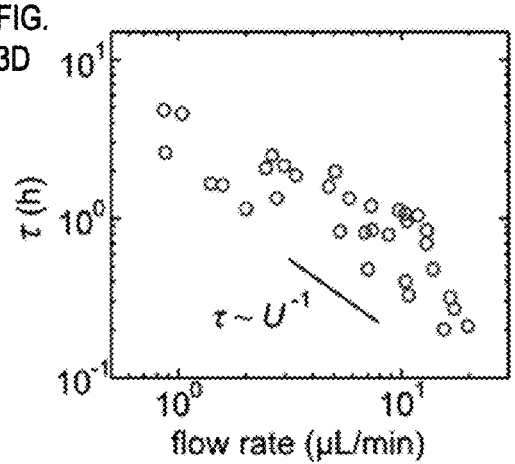
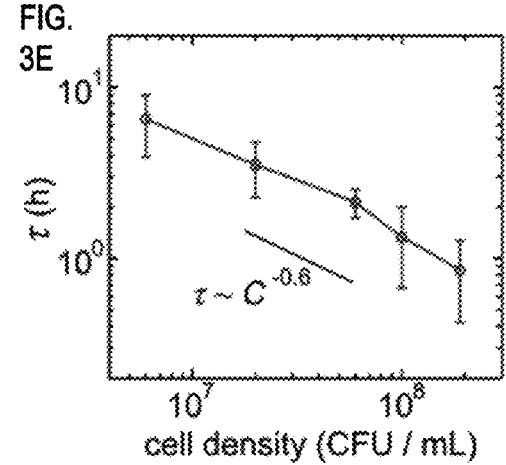

t = 71 h    t = 75.5 h    t = 78 h

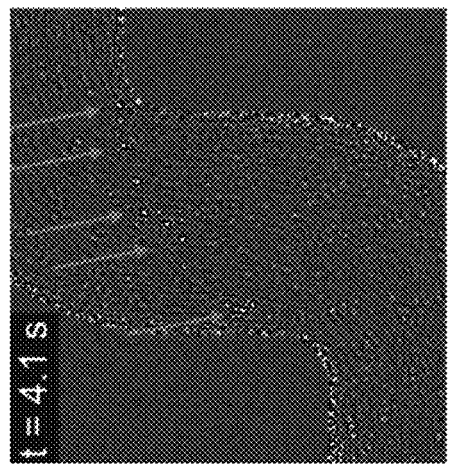
FIG. 8A t=0s
FIG. 8B t=1.0s
FIG. 8C t=4.1s
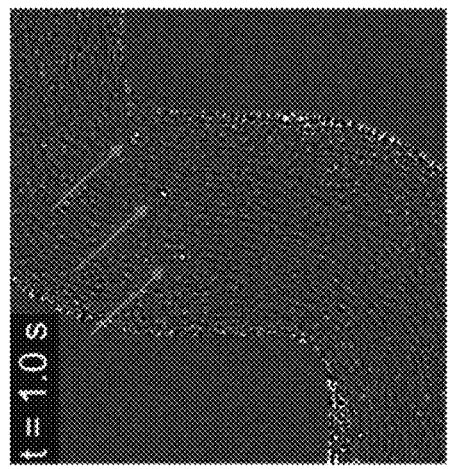
FIG. 8D t=32s
FIG. 8E t=61s
FIG. 8F t=91s
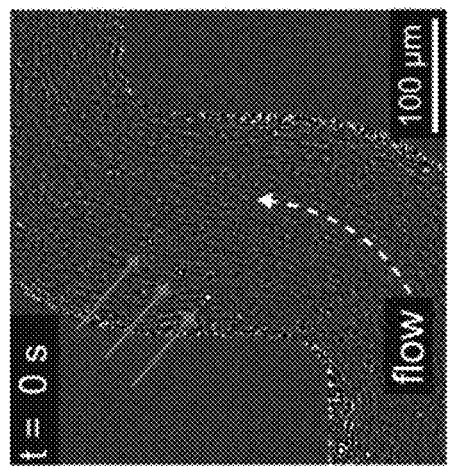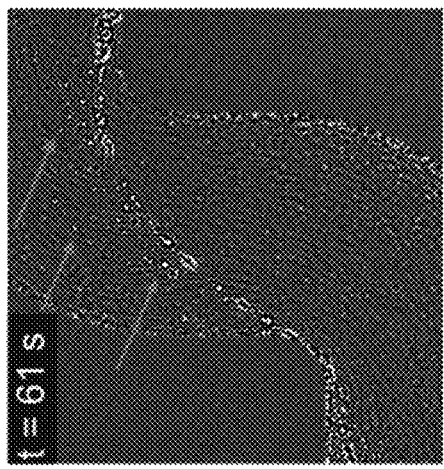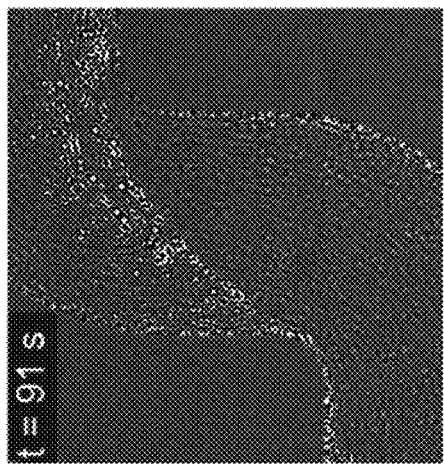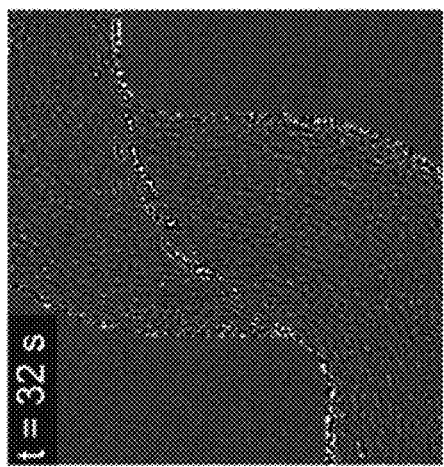

SYSTEMS AND METHODS TO DETECT BIOFILM STREAMER GROWTH AND THEIR USES

CROSS-REFERENCE TO RELATED APPLICATIONS

This application claims priority to U.S. application Ser. No. 61/923,806 filed Jan. 6, 2014, the complete disclosure of which, in its entirety, is herein incorporated by reference.

STATEMENT REGARDING FEDERALLY SPONSORED RESEARCH OR DEVELOPMENT

This invention was made with government support under National Institutes of Health (NIH) grant 5R01GM065859, and National Science Foundation (NSF) grants MCB-0343821 and MCB-1119232. The government has certain rights in this invention.

BACKGROUND

In a process referred to as quorum sensing, bacteria communicate using chemical signaling molecules called autoinducers. By monitoring increases and decreases in autoinducer concentration, quorum-sensing bacteria track changes in cell-population density and synchronously switch into and out of group behaviors. Quorum sensing allows bacteria to collectively carry out tasks that would be unsuccessful if carried out by an individual bacterium acting alone.

Both Gram-positive and Gram-negative infectious bacteria, which include human, animal, plant, and marine pathogens, use quorum sensing strategies to control virulence. Quorum sensing also controls biofilm formation. Biofilms are communities of bacterial cells adhered to surfaces and encased in a self-excreted matrix of extracellular polymeric substances. In most environments, bacteria are found predominantly in biofilms. These biofilms are also widespread in industrial systems and are associated with increased risk of infection when found in clinical environments and in indwelling medical devices. These bacterial communities can cause chronic infections in humans by colonizing, for example, medical implants, heart valves, or lungs. *Staphylococcus aureus,* a notorious human pathogen, causes some of the most common biofilm-related infections. In these environments, biofilms are highly problematic. Bacteria in biofilms are often significantly more resistant to antibiotics and antimicrobial agents. Thus, they can be very difficult to eradicate.

In settings involving flow across the biofilm, as in rivers or in all manners of industrial and medical fluid handling systems, filamentous biofilms, called streamers, can be formed. These streamers can have a dramatic effect on the biofilm environment. In rivers, for example, the biofilm streamers can increase transient storage and cycling of nutrients and can enhance the retention of suspended particles. In industrial settings, the biofilm streamers have been associated with increased issues associated with clogging and pressure drops. Although biofilms and streamers play such an important role in industrial and clinical settings, the precise mechanisms driving their formation are poorly understood. This underscores the need for a system that mimics natural formation processes and allows for screening of potential inhibitors of biofilm and biostream formation.

Additionally, bacterial infections are treated with bactericidal or bacteriostatic molecules that impede four major processes: DNA replication, transcription, translation or tetrahydrofolic acid synthesis. Existing methods for treating bacterial infection unfortunately exacerbate the growing antibiotic resistance problem because they inherently select for growth of bacteria that in turn can resist the drug. What is needed are new methods of screening for treatments that avoid selecting for drug resistant bacteria.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject.

The present invention relates to a system for measuring biofilm and/or biofilm streamers, wherein the system comprises at least one channel with an inlet, an outlet, a lumen and at least one biofilm streamer promotion element. The system comprises a fluid flowing along the channel, driven by a controlled pressure, wherein the flow rate of the fluid can be measured prior, during and/or after testing.

In some embodiments, the flow rate measuring element comprises a dish, optionally placed on an analytical balance. This measuring element can also be connected to a computer capable of measuring, for example, the weight of the effluent every few seconds.

In some embodiments, the controlled pressure is provided by a pumping element. In further embodiments, the pumping element can be, for example, gravity, a syringe, a weight, a pump or the like. In further embodiments, the pumping element is a reservoir suspended above the height of the dish. In this situation, the height differential between the reservoir and the dish, for example, can determine the controlled pressure applied to the fluid in the channel.

In other preferred embodiments, the biofilm streamer comprises microorganisms. In further embodiments, the biofilm streamer comprises microorganisms selected from the following groups: bacteria, archaea, protozoa, fungi, and algae. In further embodiments, the biofilm streamer comprises bacteria. In further embodiments, these bacteria can be, for example, pathogenic to humans, animals and/or plants. In further embodiments the biofilm streamer comprises bacteria common to industrial settings, such as, for example, industrial fluid handling processes or machinery. In still further embodiments the biofilm streamer comprises bacteria selected from the following genera: *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anabaena, Anabaenopsis, Anaerobospirillum, Anaerorhabdus, Aphanizomenon, Arachnia, Arcanobacterium, Arcobacter, Arthrobacter, Atopobium, Aureobacterium, Bacillus, Bacteroides, Balneatrix, Bartonella, Bergeyella, Bifidobacterium, Bilophila, Bordetella, Borrelia, Brachyspira, Branhamella, Brevibacillus, Brevibacterium, Brevundimonas, Brucella, Burkholderia, Buttiauxella, Butyrivibrio, Calymmatobacterium, Camesiphon, Campylobacter, Capnocytophaga, Capnylophaga, Cardiobacterium, Catonella, Cedecea, Cellulomonas, Centipeda, Chlamydia, Chlamydophila, Chromobacterium, Chryseomonas, Chyseobacterium, Citrobacter, Clostridium, Collinsella, Comamonas, Corynebacterium, Coxiella, Cryptobacterium, Cyanobacteria, Cylindrospermopsis, Delftia, Dermabacter, Dermatophilus, Desulfomonas, Desulfovibrio, Dialister,*

*Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gloeobacter, Gordona, Haemophilus, Hafnia, Hapalosiphon, Helicobacter, Helococcus, Hemophilus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptospirae, Leptotrichia, Leuconostoc, Listeria, Listonella, Lyngbya, Megasphaera, Methylobacterium, Microbacterium, Micrococcus, Microcystis, Mitsuokella, Mobiluncus, Moellerella, Moraxella, Morganella, Mycobacterium, Mycoplasma, Myroides, Neisseria, Nocardia, Nocardiopsis, Nodularia, Nostoc, Ochrobactrum, Oeskovia, Oligella, Orientia, Paenibacillus, Pantoea, Parachlamydia, Pasteurella, Pediococcus, Peptococcus, Peptostreptococcus, Phormidium, Photobacterium, Photorhabdus, Phylobacterium, Phytoplasma, Planktothrix, Plesiomonas, Porphyromonas, Prevotella, Propionibacterium, Proteus, Providencia, Pseudoanabaena, Pseudomonas, Pseudonocardia, Pseudoramibacter, Psychrobacter, Rahnella, Ralstonia, Rhodococcus, Rickettsia, Rochalimaea, Roseomonas, Rothia, Ruminococcus, Salmonella, Schizothrix, Selenomonas, Serpulina, Serratia, Shewenella, Shigella, Simkania, Slackia, Sphaerotilus, Sphingobacterium, Sphingomonas, Spirillum, Spiroplasma, Spirulina, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Trichodesmium, Tropheryma, Tsakamurella, Turicella, Umezakia, Ureaplasma, Vagococcus, Veillonella, Vibrio, Weeksella, Wolinella, Xanthomonas, Xenorhabdus, Yersinia,* and *Yokenella.* In still further embodiments the biofilm streamer comprises bacteria selected from the following species: *Acinetobacter baumannii, Actinobacillus actinomycetemcomitans, Actinobacillus pleuropneumoniae, Actinomyces bovis, Actinomyces israelii, Bacillus anthracis, Bacillus ceretus, Bacillus coagulans, Bacillus liquefaciens, Bacillus popillae, Bacillus subtilis, Bacillus thuringiensis, Bacteroides distasonis, Bacteroides fragilis, Bacteroides thetaiotaomicron, Bacteroides vulgatus, Bartonella bacilliformis, Bartonella Quintana, Beneckea parahaemolytica, Bordetella bronchiseptica, Bordetella parapertussis, Bordetella pertussis, Borelia burgdorferi, Brevibacterium lactofermentum, Brucella abortus, Brucella canis, Brucella melitensis, Brucella suis, Burkholderia cepacia, Burkholderia mallei, Burkholderia pseudomallei, Campylobacter fetus, Campylobacter jejuni, Campylobacter pylori, Cardiobacterium hominis, Chlamydia pneumoniae, Chlamydia psittaci, Chlamydia trachomatis, Chlamydophila abortus, Chlamydophila caviae, Chlamydophila felis, Chlamydophila pneumonia, Chlamydophila psittaci, Chryseobacterium eningosepticum, Clostridium botulinum, Clostridium butyricum, Clostridium coccoides, Clostridium difficile, Clostridium leptum, Clostridium tetani, Corynebacterium xerosis, Cowdria ruminantium, Coxiella burnetii, Edwardsiella tarda, Ehrlichia sennetsu, Eikenella corrodens, Elizabethkingia meningoseptica, Enterobacter aerogenes, Enterobacter cloacae, Enterococcus faecalis, Escherichia coli, Escherichia hirae, Flavobacterium meningosepticum, Fluoribacter bozemanae, Francisella tularensis, Francisella tularensis biovar Tularensis, Francisella tularensis* subsp. *Holarctica, Francisella tularensis* subsp. *nearctica, Francisella tularensis* subsp. *Tularensis, Francisella tularensis* var. *palaearctica, Fudobascterium nucleatum, Fusobacterium necrophorum, Haemophilus ducreyi, Haemophilus influenzae, Helicobacter pylori, Kingella kingae, Klebsiella mobilis, Klebsiella oxytoca, Klebsiella pneumoniae, Lactobacillus acidophilus, Lactobacillus casei, Lactobacillus hilgardii, Lactobacillus pentosus, Lactobacillus plantarum, Lactobacillus rhamnosus, Lactococcus lactis, Legionella bozemanae* corrig., *Legionella pneumophila, Leptospira alexanderi, Leptospira borgpetersenii, Leptospira fainei, Leptospira inadai, Leptospira interrogans, Leptospira kirschneri, Leptospira noguchii, Leptospira santarosai, Leptospira weilii, Leuconostoc lactis, Leuconostoc oenos, Listeria ivanovii, Listeria monocytogenes, Moraxella catarrhalis, Morganella morganii, Mycobacterium africanum, Mycobacterium avium, Mycobacterium avium* subspecies *paratuberculosis, Mycobacterium bovis, Mycobacterium bovis* strain BCG, *Mycobacterium intracellulare, Mycobacterium kansasii, Mycobacterium leprae, Mycobacterium marinum, Mycobacterium tuberculosis, Mycobacterium typhimurium, Mycobacterium ulcerans, Mycoplasma hominis, Mycoplasma mycoides, Mycoplasma pneumoniae, Neisseria gonorrhoeae, Neisseria meningitidis, Neorickettsia sennetsu, Nocardia asteroides, Orientia tsutsugamushi, Pasteurella haemolytica, Pasteurella multocida, Plesiomonas shigelloides, Propionibacterium acnes, Proteus mirabilis, Proteus morganii, Proteus penneri, Proteus rettgeri, Proteus vulgaris, Providencia alcalifaciens, Providencia rettgeri, Pseudomonas aeruginosa, Pseudomonas mallei, Pseudomonas pseudomallei, Pyrococcus abyssi, Rickettsia akari, Rickettsia canadensis, Rickettsia canadensis corrig, Rickettsia conorii, Rickettsia montanensis, Rickettsia montanensis* corrig., *Rickettsia prowazekii, Rickettsia rickettsii, Rickettsia sennetsu, Rickettsia tsutsugamushi, Rickettsia typhi, Rochalimaea quintana, Salmonella arizonae, Salmonella choleraesuis* subsp. *arizonae, Salmonella enterica* subsp. *Arizonae, Salmonella enteritidis, Salmonella paratyphi, Salmonella typhi, Salmonella typhimurium, Selenomonas nominantium, Selenomonas ruminatium, Serratia marcescens, Shigella boydii, Shigella dysenteriae, Shigella flexneri, Shigella sonnei, Spirillum minus, Staphylococcus aureus, Staphylococcus epidermidis, Staphylococcus equi, Staphylococcus lugdunensis, Stenotrophomonas maltophila, Streptobacillus moniliformis, Streptococcus agalactiae, Streptococcus bovis, Streptococcus ferus, Streptococcus pneumoniae, Streptococcus pyogenes, Streptococcus viridans, Streptomyces ghanaenis, Streptomyces hygroscopicus, Streptomyces phaechromogenes, Treponema carateum, Treponema denticola, Treponema pallidum, Treponema pertenue, Vibrio cholerae, Vibrio parahaemolyticus, Vibrio vulnificus, Xanthomonas maltophilia, Yersinia enterocolitica, Yersinia pestis, Yersinia pseudotuberculosis,* and *Zymomonas mobilis.* In still further embodiments the biofilm streamer comprises bacteria from the class of bacteria known as Fusospirochetes. In further embodiments the biofilm streamer comprises fungi. In still further embodiments, the biofilm streamer comprises fungi selected from the following genera: *Candida, Saccharomyces,* and *Cryptococcus.*

Such pathogenic bacteria can cause bacterial infections and disorders related to such infections that include, but are not limited to, the following: acne, rosacea, skin infection, pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Peptostreptococcus* spp. or *Pseudomonas* spp.; pharyngitis, rheumatic fever, and glomerulonephritis related to infection by *Streptococcus pyo-*

*genes,* Groups C and G *streptococci, Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive *staphylococci* (i.e., *S. epidermidis, S. hemolyticus,* etc.), *S. pyogenes, S. agalactiae, Streptococcal* groups C-F (minute-colony *streptococci), viridans streptococci, Corynebacterium* spp., *Clostridium* spp., or *Bartonella henselae;* uncomplicated acute urinary tract infections related to infection by *S. saprophyticus* or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Nesseria gonorrheae;* toxin diseases related to infection by *S. aureus* (food poisoning and Toxic shock syndrome), or Groups A, S, and C *streptococci;* ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare;* gastroenteritis related to infection by *Campylobacter jejuni;* odontogenic infection related to infection by *viridans streptococci;* persistent cough related to infection by *Bordetella pertussis;* gas gangrene related to infection by *Clostridium perfringens* or *Bacteroides* spp.; skin infection by *S. aureus, Propionibacterium* acne; atherosclerosis related to infection by *Helicobacter pylori* or *Chlamydia pneumoniae;* or the like.

In certain embodiments a biofilm-related disorder is selected from the group including pneumonia, cystic fibrosis, otitis media, chronic obstructive pulmonary disease, and a urinary tract infection and combinations thereof. In other embodiments, the biofilm-related disorder is a medical device-related infection. In further embodiments, the biofilm-related disorder is a periodontal disease, such as gingivitis, periodontitis or breath malodor. In still further embodiments, the biofilm-related disorder is caused by bacteria. In some embodiments, the bacteria are Gram-negative or Gram-positive bacteria. Non-limiting examples of biofilm-related disorders include otitis media, prostatitis, cystitis, bronchiectasis, bacterial endocarditis, osteomyelitis, dental caries, periodontal disease, infectious kidney stones, acne, Legionnaire's disease, chronic obstructive pulmonary disease (COPD), and cystic fibrosis. In one specific example, subjects with cystic fibrosis display an accumulation of biofilm in the lungs and digestive tract. Subjects afflicted with COPD, such as emphysema and chronic bronchitis, display a characteristic inflammation of the airways wherein airflow through such airways, and subsequently out of the lungs, is chronically obstructed. Biofilm-related disorders can also encompass infections derived from implanted/inserted devices, medical device-related infections, such as infections from biliary stents, orthopedic implant infections, and catheter-related infections (kidney, vascular, peritoneal). An infection can also originate from sites where the integrity of the skin and/or soft tissue has been compromised. Non-limiting examples include dermatitis, ulcers from peripheral vascular disease, a burn injury, and trauma.

In preferred embodiments, the system is mounted to a glass coverslip. This glass coverslip can, for example, can allow the biofilm and/or biofilm streamer growth and morphology changes to be directly imaged using a microscope. In other preferred embodiments, the microscope used in the described system is a confocal laser scanning microscope or an epifluorescence microscope.

In some embodiments, the channel is at least 200 µm wide. In further embodiments, the channel is at least 1 mm wide. In still further embodiments, the channel is at least 10 µm wide, at least 20 µm wide, at least 30 µm wide, at least 40 µm wide, at least 50 µm wide, at least 60 µm wide, at least 70 µm wide, at least 80 µm wide, at least 90 µwide, at least 100 µm wide, at least 125 µwide, at least 150 µm wide, at least 175 µm wide, at least 200 µm wide, at least 300 µm wide, at least 400 µm wide, at least 500 µm wide, at least 600 µm wide, at least 700 µm wide, at least 800 µm wide, at least 900 µm wide, at least 1 mm wide, at least 2 mm wide, at least 3 mm wide, at least 4 mm wide, at least 5 mm wide, at least 6 mm wide, at least 7 mm wide, at least 8 mm wide, at least 9 mm wise, and/or at least 10 mm wide. In some embodiments, the channel is at least 90 µm high. In still further embodiments, the channel is at least 10 µm high, at least 20 µm high, at least 30 µm high, at least 40 µm high, at least 50 µm high, at least 60 µm high, at least 70 µm high, at least 80 µm high, at least 90 µm high, at least 100 µm high, at least 200 µm high, at least 300 µm high, at least 400 µm high, at least 500 µm high, at least 600 µm high, at least 700 µm high, at least 800 µm high, at least 900 µm high, and/or at least 1000 µm high. In further embodiments, the channel is at least 200 µm wide and 90 µm high. In other preferred embodiments, multiple channels exist which are identical in size. In other preferred embodiments, the multiple channels are of different sizes. In other embodiments, the channel may be an enclosed hollow tube. In other embodiments, the cross section of the tube may be of any suitable geometry as is known by those of skill in the art. In further embodiments, the cross section is circular, oval, square, rectangular and/or irregularly shaped. In further embodiments, the tube may have a constant cross-sectional area and/or it may be variable (e.g. it may constrict in certain areas and/or expand in others). In other embodiments, the cross section of the channel may change shape along its length. In still further embodiments, the channel may be a depression, gutter, groove and/or furrow. This depression may be shallow, deep, narrow and/or wide. In still further embodiments, the channel may be provided by the gap between two parallel flat planar surfaces placed close together. In still further embodiments, the channel may be part of a larger device or machine. In other embodiments, the channel may be a fluid flow conduit in an implantable medical device. In still further embodiments, the channel may be a fluid flow conduit in machinery used in industrial processes. In some embodiments, the channel may be very small (i.e. just large enough for fluid and bacterial cells to flow through). In some embodiments, the channel may be very large (i.e. the large culverts and pools used in a waste water treatment facility.) In still further embodiments, the channel is circular. In still further embodiments, the channel may be a pipe, a cooling tower, medical devices, and/or other industrial fluid handling machinery.

In some embodiments, the channel comprises at least one biofilm streamer promotion element. In further embodiments, the channel has at least 2, 3, 4, 5, 6, 7, 8, 9, 10, 11, 12, 13, 14, 15, 16, 17, 18, 19, 20, 25, 30, 35, 40, 45, 50, 60, 70, 80, 90 and/or 100 biofilm streamer promotion elements.

In further embodiments, the biofilm streamer promotion element is a curved channel, a channel with at least one turn, a channel with at least one corner, an edge projecting into the lumen of the channel, a mound projecting into the lumen of the channel, a channel with roughened surfaces, and/or one or more objects placed within the channel lumen.

In further embodiments, the channel has at least 2, 3, 4, 5, 6, 7, 8, 9, 10, 11, 12, 13, 14, 15, 16, 17, 18, 19, 20, 25, 30, 35, 40, 45, 50, 60, 70, 80, 90 and/or 100 turns. In further embodiments, the channel has at least 2, 3, 4, 5, 6, 7, 8, 9, 10, 11, 12, 13, 14, 15, 16, 17, 18, 19, 20, 25, 30, 35, 40, 45, 50, 60, 70, 80, 90 and/or 100 edges projecting into the lumen of the channel. In further embodiments, the channel has at least 2, 3, 4, 5, 6, 7, 8, 9, 10, 11, 12, 13, 14, 15, 16, 17, 18, 19, 20, 25, 30, 35, 40, 45, 50, 60, 70, 80, 90 and/or 100 mounds projecting into the lumen of the channel. In further embodiments, the channel has at least 2, 3, 4, 5, 6, 7, 8, 9, 10, 11, 12, 13, 14, 15, 16, 17, 18, 19, 20, 25, 30, 35, 40, 45, 50, 60, 70, 80, 90 and/or 100 roughened surfaces. In further embodiments, the channel has at least 2, 3, 4, 5, 6, 7, 8, 9, 10, 11, 12, 13, 14, 15, 16, 17, 18, 19, 20, 25, 30, 35, 40, 45, 50, 60, 70, 80, 90 and/or 100 objects placed with the channel lumen.

In further embodiments, the channel has at least 2 corners, at least 3 corners, at least 4 corners, at least 5 corners, at least 6 corners, at least 7 corners, at least 8 corners, at least 9 corners, at least 10 corners, at least 11 corners, at least 12 corners, at least 13 corners, at least 14 corners, at least 15 corners, at least 16 corners, at least 17 corners, at least 18 corners, at least 19 corners, at least 20 corners, at least 25 corners, at least 30 corners, at least 35 corners, and/or at least 36 corners. In still further embodiments, the channel has 1 turn about every 100 µm, every 200 µm, every 300 µm, every 400 µm, every 500 µm, every 600 µm, every 700 µm, every 800 µm, 900 µm, and/or every 1000 µm.

Additionally embodiments include a combination of any of these biofilm streamer promotion elements (e.g., turns, corners, edges, mounds, roughened surfaces, and/or objects) in the channel.

In still further embodiments, the biofilm streamer promotion element is NAFION® granules placed within the channel lumen. In further embodiments, the biofilm streamer promotion element is glass beads. In further embodiments, the biofilm streamer promotion element is sand particles. In further embodiments, the biofilm streamer promotion element is a welded polypropylene feed spacer mesh. In a further embodiment, the biofilm streamer promotion element is a stent. In still further embodiments the biofilm streamer promotion element is a bare-metal stent.

In some embodiments, the fluid in the channel has a laminar flow. In further embodiments, the flow of the fluid is characterized by a Reynolds number of less than 2000, of less than 1500, of less than 1000, of less than 750, of less than 500, of less than 400, of less than 300, of less than 200, of less than 100, of less than 50, of less than 25, of less than 10, of less than 5, of less than 4, of less than 3, of less than 2, and/or of less than 1.

In some embodiments, the fluid in the channel has a turbulent flow. In further embodiments, the flow of the fluid is characterized by a Reynolds number of greater than 2000.

In some embodiments, the fluid in the channel has shear stress. In further embodiments, the shear stress is characterized by a number between 0.01 and 100 Pa, between 0.01 and 90 Pa, between 0.01 and 80 Pa, between 0.01 and 70 Pa, between 0.01 and 60 Pa, between 0.01 and 50 Pa, between 0.01 and 40 Pa, between 0.01 and 30 Pa, between 0.01 and 20 Pa, between 0.01 and 10 Pa, between 0.02 and 10 Pa, between 0.03 and 10 Pa, between 0.04 and 10 Pa, between 0.05 and 10 Pa, between 0.06 and 10 Pa, between 0.07 and 10 Pa, between 0.08 and 10 Pa, between 0.09 and 10 Pa, between 0.1 and 10 Pa, between 0.02 and 100 Pa, between 0.03 and 100 Pa, between 0.04 and 100 Pa, between 0.05 and 100 Pa, between 0.06 and 100 Pa, between 0.07 and 100 Pa, between 0.08 and 100 Pa, between 0.09 and 100 Pa, between 0.1 and 100 Pa, between 0.1 and 90 Pa, between 0.1 and 80 Pa, between 0.1 and 70 Pa, between 0.1 and 60 Pa, between 0.1 and 50 Pa, between 0.1 and 40 Pa, between 0.1 and 30 Pa, between 0.1 and 20 Pa, between 0.02 and 90 Pa, between 0.03 and 80 Pa, between 0.04 and 70 Pa, between 0.05 and 60 Pa, between 0.06 and 50 Pa, between 0.07 and 40 Pa, between 0.08 and 30 Pa, and/or between 0.09 and 20 Pa.

In some embodiments, the system further comprises a three-inlet port capable of being opened and closed by multilayer microfluidic gates.

The present invention also relates to a method of measuring biofilm and/or biofilm streamer formation, growth, and/or morphology changes using the system of the invention, wherein the method comprises passing a fluid through the system in the presence or absence of a test compound or an industrial material and monitoring the flow rate over time. For example, by determining the time until clogging (T) and the duration of the clogging transition (τ) or by imaging the formation, growth or morphology changes of the biofilm and/or biofilm streamer, one can determine the ability of the compound or industrial material to inhibit or enhance biofilm and/or biofilm streamer growth. Other embodiments include a method of screening compounds that can inhibit, promote or affect biofilm and/or biofilm streamers.

BRIEF DESCRIPTION OF THE DRAWINGS

Embodiments are illustrated by way of example and not limitation in the figures of the accompanying drawings, in which like references indicate similar elements and in which:

FIG. 1A shows a model microfluidic channel, which is 200 µm wide and 90 µm high. FIG. 1B shows measurement of flow rate versus time. The flow rate through this channel only changes slowly during biofilm buildup on the walls of the channel for the time period T. Channel walls are indicated by dashed white lines, and cells constitutively express gfp. Biofilm streamers expand rapidly and cause clogging over a short time τ.

FIG. 2A shows a semilogarithmic plot of the accumulation of cells on the walls, measured via GFP fluorescence. Different colors represent data from n=10 independent experiments. FIG. 2B shows that T depends on flow rate, and can be prolonged by slowing growth with a low concentration of the growth-inhibitor tetracycline (tet). FIG. 2C shows that tetracycline has no effect on τ. FIG. 2D shows the results of an experiment wherein cells expressing gfp are flowed through the channel at a rate 18.1±0.05 µL/min for the first 43 h, then are subsequently exchanged to contain only cells producing the red fluorescent protein mCherry. Biofilm streamers are exclusively composed of red cells, whereas very few red cells attach to the resident green biofilm on the wall, indicating that streamers consist of cells that were transported to the eventual clogging site by flow.

FIGS. 3A-3E show that biofilm filaments form a sieve-like network that captures cells flowing through. FIG. 3A shows that a model based on a nonporous biofilm streamer oriented transverse to the flow direction predicts slow growth rates for the streamer radius R. FIG.3B shows that a model based on a porous streamer, which grows by capturing cells that flow through it, predicts exponential growth for R. FIG.3C shows an image of the biofilm during the clogging transition for an initial flow rate 1.5±0.05 µL/min. $P.$ $aeruginosa$ cells are shown in red, EPS is visualized with green fluorescent dyes conjugated to polysaccharide-binding lectins and a green fluorescent DNA stain. Yellow regions result from the superposition of green and red channels. White arrows point to smaller biofilm streamers that form a network. The thick streamer structures are interspersed with dark regions, indicating that these structures are porous. The porosity is further illustrated by FIGS. 8A- 8F. FIG.3D shows the clogging duration $\tau$ for different flow rates (which are proportional to U, the average flow speed before streamers emerge) at a fixed concentration of ≈2×10⁸ cfu/mL, corresponding to midlogarithmic-phase growth. FIG.3E shows $\tau$ for different cell concentrations at a fixed flow rate of 4.8±0.8 µL/min. Error bars: SD of n=8 independent measurements.

FIGS. 4A and 4B show a comparison of the time until clogging (T) and the duration of the clogging transition ($\tau$) for different mutants: $\Delta pelA$ lacks the major component of the EPS, $\Delta flgK$ is nonmotile due to an incomplete flagellum (21), $\Delta pilC$ has no type IV pili, and $\Delta lasR$ lacks the quorum sensing master regulator. FIG.4C shows that $\Delta pelA$ produces no significant biofilm during 210 h of observation. FIG.4D shows that $\Delta flgK$ produces biofilm streamers similar to the wild type. FIG.4E shows that $\Delta pilC$ forms no streamers, but does form thick biofilms on the walls of the channel. FIG.4F shows that $\Delta lasR$ forms biofilms on the walls of the channel, which detach, slowly deform, and reattach to clog the channel. The image lookup table is the same for FIGS. 4C-4F. Scale bars: 200 µm.

FIG. 5A shows a time series of biofilm buildup in a 3D soil-like porous material made from transparent Nafion® granules (outlined by red dashed lines). Green indicates $P.$ $aeruginosa$ cells constitutively expressing gfp. Arrows point toward streamers, which are heterogeneous in thickness at this magnification. FIG. 5B shows that networks of biofilm streamers form in a feed spacer mesh, which is a component of spiral-wound reverse osmosis water filters. The image is a maximum-intensity projection of a confocal z-stack, which visualizes biofilms on the surface of the mesh, located outside the white dashed lines. FIG. 5C shows that biofilm streamers form in bare-metal stents. White arrows point to streamers; green arrows point to wire mesh of the stent. The image is stitched together from the maximum intensity projections of 83 z-stacks. A false-color scheme is used to illustrate that different color intensity scales were used for visualizing the stent surface and the streamers because the fluorescence from the stent surface was significantly brighter due to the large amount of biomass on the surface. The resulting two images of the stent surface and the streamers were overlaid, giving the displayed image. Green indicates $P.$ $aeruginosa$ cells constitutively expressing gfp. Arrows point toward streamers, which are heterogeneous in thickness and biomass at this magnification.

FIG.7A shows a model where biofilm (green) forms as a thin film of thickness $\epsilon\rho$ on the walls of a cylindrical channel with radius $\rho$. FIG. 7B shows a model where biofilm forms as a cylindrical streamer that is coaxial with the channel.

FIGS. 8A-8F show a biofilm streamer initiation image sequence. Images were acquired at 30 frames per second using bright-field microscopy, and a background image was subtracted to visualize newly appearing structures such as streamers. The background image is made from the average of the 10 images taken 5 s before each image shown. FIG. 8A shows that a thin streamer has formed, originating from the left corner. The streamer is not yet attached to the right corner. It appears to mostly consist of EPS, and only three cell/EPS clusters are visible. Red arrows point to these clusters. FIG 8B shows that the streamer has attached to the right corner, forming a biofilm bridge between the corners. The red arrows point to the same three clusters as in FIG.8A, indicating that the streamer is now largely transverse to the flow direction in contrast with FIG.8A. EPS: extracellular polymeric substances. FIG. 8C shows that additional cell/EPS clusters attach to the streamer, as indicated by the red arrows. At this stage, the streamer is flexible and vibrates in the flow. FIG. 8D shows that the streamer has accumulated additional biomass and is less flexible. FIG. 8E shows that small secondary streamers are dragged out of the main streamer and appear to form a sieve-like network. Red arrows point to some of these secondary streamers. FIG.8F shows that the mesh of streamers that appeared in FIG.8E has accumulated more biomass and new secondary streamers emerge.

FIG. 12A shows that the ΔflgK mCherry strain forms streamers after 5 h. FIG.12B shows that the ΔpilC mCherry strain forms streamers after 7 h. FIG. 12C shows that the ΔlasR mCherry strain forms streamers after 16 h. FIG. 12D shows that a part of the PA14-gfp biofilm detached from the wall at 17.5 h and triggered streamer formation of the ΔpelA mCherry strain. Scale bar: 200 µm.

FIG. 13A shows the results from simultaneously monitoring the OD600 and CFU concentration of *P. aeruginosa* wild-type cultures in n=6 independent reservoirs over time. Both measurements remain roughly constant for ~3 d. FIGS. 13B and 13C show that the clogging duration τ and time of clogging T are similar for experiments in which the culture in the reservoir is exchanged every 24 h, compared with experiments in which the culture is not exchanged.

DETAILED DESCRIPTION

A. Definitions

Figure 1A:
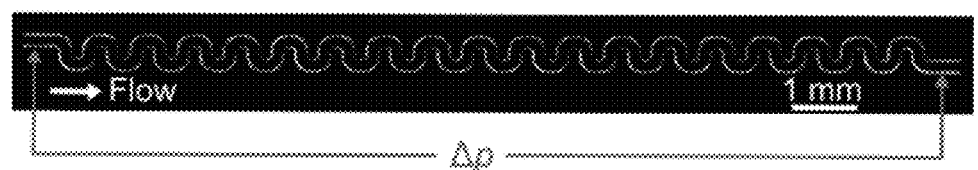
FIGS. 1A and 1B show that biofilm streamers cause rapid and sudden clogging.

Unless defined otherwise, all technical and scientific terms used herein have the same meaning as commonly understood by those of ordinary skill in the art, such as in the arts of peptide chemistry, cell culture, nucleic acid chemistry, and biochemistry. Standard techniques are used for molecular biology, genetic and biochemical methods (see Sambrook et al., Molecular Cloning: A Laboratory Manual, 3$^{rd}$ ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

In the present invention, "bacteria" are defined as any one of a large domain of single-celled prokaryotic microorganisms. As used herein, bacteria include any that are known to those of ordinary skill in the art and any that may be discovered. Preferred examples of bacteria are those known to be pathogenic to humans, animals or plants. Other preferred examples include those known to cause undesirable contamination and/or clogging of industrial flow systems. Still other preferred examples of bacteria include those known to infect implanted medical devices (pumps, stents, artificial joints, screws, rods, and the like). Further preferred examples of bacteria include those capable of forming biofilms and/or biostreamers. In the laboratory, bacteria are usually grown as planktonic cells in shaken suspensions, which differs dramatically from the natural environments of most microbes. In their natural habitats, bacteria often live in biofilms. Further preferred examples include bacteria selected from the following genera: *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anabaena, Anabaenopsis, Anaerobospirillum, Anaerorhabdus, Aphanizomenon, Arachnia, Arcanobacterium, Arcobacter, Arthrobacter, Atopobium, Aureobacterium, Bacillus, Bacteroides, Balneatrix, Bartonella, Bergeyella, Bifidobacterium, Bilophila, Bordetella, Borrelia, Brachyspira, Branhamella, Brevibacillus, Brevibacterium, Brevundimonas, Brucella, Burkholderia, Buttiauxella, Butyrivibrio, Calymmatobacterium, Camesiphon, Campylobacter, Capnocytophaga, Capnylophaga, Cardiobacterium, Catonella, Cedecea, Cellulomonas, Centipeda, Chlamydia, Chlamydophila, Chromobacterium, Chryseomonas, Chyseobacterium, Citrobacter, Clostridium, Collinsella, Comamonas, Corynebacterium, Coxiella, Cryptobacterium, Cyanobacteria, Cylindrospermopsis, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gloeobacter, Gordona, Haemophilus, Hafnia, Hapalosiphon, Helicobacter, Helococcus, Hemophilus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptospirae, Leptotrichia, Leuconostoc, Listeria, Listonella, Lyngbya, Megasphaera, Methylobacterium, Microbacterium, Micrococcus, Microcystis, Mitsuokella, Mobiluncus, Moellerella, Moraxella, Morganella, Mycobacterium, Mycoplasma, Myroides, Neisseria, Nocardia, Nocardiopsis, Nodularia, Nostoc, Ochrobactrum, Oeskovia, Oligella, Orientia, Paenibacillus, Pantoea, Parachlamydia, Pasteurella, Pediococcus, Peptococcus, Peptostreptococcus, Phormidium, Photobacterium, Photorhabdus, Phyllobacterium, Phytoplasma, Planktothrix, Plesiomonas, Porphyromonas, Prevotella, Propionibacterium, Proteus, Providencia, Pseudoanabaena, Pseudomonas, Pseudonocardia, Pseudoramibacter, Psychrobacter, Rahnella, Ralstonia, Rhodococcus, Rickettsia, Rochalimaea, Roseomonas, Rothia, Ruminococcus, Salmonella, Schizothrix, Selenomonas, Serpulina, Serratia, Shewenella, Shigella, Simkania, Slackia, Sphaerotilus, Sphingobacterium, Sphingomonas, Spirillum, Spiroplasma, Spirulina, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Trichodesmium, Tropheryma, Tsakamurella, Turicella, Umezakia, Ureaplasma, Vagococcus, Veillonella, Vibrio, Weeksella, Wolinella, Xanthomonas, Xenorhabdus, Yersinia,* and *Yokenella.* Further preferred examples include bacteria selected from the following species: *Acinetobacter baumannii, Actinobacillus actinomycetemcomitans, Actinobacillus pleuropneumoniae, Actinomyces bovis, Actinomyces israelii, Bacillus anthracis, Bacillus ceretus, Bacillus coagulans, Bacillus liquefaciens, Bacillus popillae, Bacillus subtilis,*

*Bacillus thuringiensis, Bacteroides distasonis, Bacteroides fragilis, Bacteroides thetaiotaomicron, Bacteroides vulgatus, Bartonella bacilliformis, Bartonella Quintana, Beneckea parahaemolytica, Bordetella bronchiseptica, Bordetella parapertussis, Bordetella pertussis, Borelia burgdorferi, Brevibacterium lactofermentum, Brucella abortus, Brucella canis, Brucella melitensis, Brucella suis, Burkholderia cepacia, Burkholderia mallei, Burkholderia pseudomallei, Campylobacter fetus, Campylobacter jejuni, Campylobacter pylori, Cardiobacterium hominis, Chlamydia pneumoniae, Chlamydia psittaci, Chlamydia trachomatis, Chlamydophila abortus, Chlamydophila caviae, Chlamydophila felis, Chlamydophila pneumonia, Chlamydophila psittaci, Chryseobacterium eningosepticum, Clostridium botulinum, Clostridium butyricum, Clostridium coccoides, Clostridium difficile, Clostridium leptum, Clostridium tetani, Corynebacterium xerosis, Cowdria ruminantium, Coxiella burnetii, Edwardsiella tarda, Ehrlichia sennetsu, Eikenella corrodens, Elizabethkingia meningoseptica, Enterobacter aerogenes, Enterobacter cloacae, Enterococcus faecalis, Escherichia coli, Escherichia hirae, Flavobacterium meningosepticum, Fluoribacter bozemanae, Francisella tularensis, Francisella tularensis biovar Tularensis, Francisella tularensis* subsp. *Holarctica, Francisella tularensis* subsp. *nearctica, Francisella tularensis* subsp. *Tularensis, Francisella tularensis* var. *palaearctica, Fudobascterium nucleatum, Fusobacterium necrophorum, Haemophilus ducreyi, Haemophilus influenzae, Helicobacter pylori, Kingella kingae, Klebsiella mobilis, Klebsiella oxytoca, Klebsiella pneumoniae, Lactobacillus acidophilus, Lactobacillus casei, Lactobacillus hilgardii, Lactobacillus pentosus, Lactobacillus plantarum, Lactobacillus rhamnosus, Lactococcus lactis, Legionella bozemanae corrig., Legionella pneumophila, Leptospira alexanderi, Leptospira borgpetersenii, Leptospira fainei, Leptospira inadai, Leptospira interrogans, Leptospira kirschneri, Leptospira noguchii, Leptospira santarosai, Leptospira weilii, Leuconostoc lactis, Leuconostoc oenos, Listeria ivanovii, Listeria monocytogenes, Moraxella catarrhalis, Morganella morganii, Mycobacterium africanum, Mycobacterium avium, Mycobacterium avium* subspecies *paratuberculosis, Mycobacterium bovis, Mycobacterium bovis* strain BCG, *Mycobacterium intracellulare, Mycobacterium kansasii, Mycobacterium leprae, Mycobacterium marinum, Mycobacterium tuberculosis, Mycobacterium typhimurium, Mycobacterium ulcerans, Mycoplasma hominis, Mycoplasma mycoides, Mycoplasma pneumoniae, Neisseria gonorrhoeae, Neisseria meningitidis, Neorickettsia sennetsu, Nocardia asteroides, Orientia tsutsugamushi, Pasteurella haemolytica, Pasteurella multocida, Plesiomonas shigelloides, Propionibacterium acnes, Proteus mirabilis, Proteus morganii, Proteus penneri, Proteus rettgeri, Proteus vulgaris, Providencia alcalifaciens, Providencia rettgeri, Pseudomonas aeruginosa, Pseudomonas mallei, Pseudomonas pseudomallei, Pyrococcus abyssi, Rickettsia akari, Rickettsia canadensis, Rickettsia canadensis corrig, Rickettsia conorii, Rickettsia montanensis, Rickettsia montanensis corrig, Rickettsia prowazekii, Rickettsia rickettsii, Rickettsia sennetsu, Rickettsia tsutsugamushi, Rickettsia typhi, Rochalimaea quintana, Salmonella arizonae, Salmonella choleraesuis* subsp. *arizonae, Salmonella enterica* subsp. *Arizonae, Salmonella enteritidis, Salmonella paratyphi, Salmonella typhi, Salmonella typhimurium, Selenomonas nominantium, Selenomonas ruminatium, Serratia marcescens, Shigella boydii, Shigella dysenteriae, Shigella flexneri, Shigella sonnei, Spirillum minus, Staphylococcus aureus, Staphylococcus epidermidis, Staphylococcus equi, Staphylococcus lugdunensis, Stenotrophomonas maltophila, Streptobacillus moniliformis, Streptococcus agalactiae, Streptococcus bovis, Streptococcus ferus, Streptococcus pneumoniae, Streptococcus pyogenes, Streptococcus viridans, Streptomyces ghanaenis, Streptomyces hygroscopicus, Streptomyces phaechromogenes, Treponema carateum, Treponema denticola, Treponema pallidum, Treponema pertenue, Vibrio cholerae, Vibrio parahaemolyticus, Vibrio vulnificus, Xanthomonas maltophilia, Yersinia enterocolitica, Yersinia pestis, Yersinia pseudotuberculosis,* and *Zymomonas mobilis.* Further preferred examples include bacteria selected from the class of bacteria known as Fusospirochetes.

In the present invention, "fungi" are defined as any one of a large domain of single-celled eucharyotic microorganisms such as yeasts. As used herein, fungi include any that are known to those of ordinary skill in the art and any that may be discovered. Preferred examples of fungi are those known to be pathogenic to humans, animals or plants. Other preferred examples include those known to cause undesirable contamination and/or clogging of industrial flow systems. Still other preferred examples of fungi include those known to infect implanted medical devices (pumps, stents, artificial joints, screws, rods, and the like). Further preferred examples of fungi include those capable of forming biofilms and/or biostreamers. In the laboratory, fungi are usually grown as planktonic cells in shaken suspensions, which differs dramatically from the natural environments of most microbes. In their natural habitats, fungi often live in biofilms. Further preferred examples include fungi selected from the genera: *Candida, Saccharomyces,* and *Cryptococcus.*

In the present invention, "biofilms" are defined as sessile bacterial and/or fungal communities that occupy moist surfaces and can cause chronic and medical device-associated infections. Biofilms are tightly packed, surface-associated assemblies of bacteria and/or fungi that are bound together by extracellular polymeric substances (4, 5). Biofilms are attached to the surface all along the edges, including the bottom edge, of the biofilm. Although bacterial biofilms are desirable in waste-water treatment (6), biofilms primarily cause undesirable effects such as chronic infections or clogging of industrial flow systems (1-3). Cells in biofilms display many behavioral differences from planktonic cells, such as a 1,000-fold increase in tolerance to antibiotics (7, 8), an altered transcriptome (9-11), and spatially heterogeneous metabolic activity (12, 13). Some of these physiological peculiarities of biofilm-dwelling cells may be due to strong gradients of nutrients and metabolites, which also affect biofilm morphology and composition (14, 15).

In the present invention, "biofilm streamers" are defined as biofilms that have been partially detached from the surface upon which the biofilm is growing. Under conditions of flow in the presence of available biofilm promotion element(s) (e.g., curves, corners, bends, etc.), the flow partially detaches the extra cellular matrix off of the substrate along with cells that were in it already and is suspended in the liquid attached only at its edges. The detached biofilm forms filaments or streamers in the flowing liquid. The streamer is then able to capture other flowing debris and cells in order to continue growing. Thus, biofilms grow by cellular division, while biofilm streamers grow both by cell division as well as cellular capture of passing cells in the flow.

In the present invention, "biofilm growth" is defined as the expansion of the surface-attached biofilm over time, whether through cell division or through attachment of additional cells to the surface from the surrounding liquid.

As used herein, this growth includes expansion laterally over available surfaces as well as expansion through thickening of the biofilm layer.

In the present invention, "biofilm morphology" is defined as the physical composition or shape of the biofilm. As used in the invention, biofilm morphology may change over time. These changes may be in composition of the extracellular matrix, in the composition of bacteria and/or fungi in the biofilm, or in the shape of the biofilm. Biofilm growth would be an example of a change in biofilm morphology. Another example of a change in biofilm morphology would be the flow induced formation of biofilm streamers.

In the present invention, "biofilm streamer growth" is defined as the expansion of the biofilm streamer over time. As used herein, this expansion may be in the length of the biofilm streamer filaments and/or in the thickness of the biofilm streamer. This growth may be through cell division and/or through capture of additional cells, extracellular matrix, and/or debris from the surrounding liquid.

In the present invention, "biofilm streamer morphology" is defined as the physical composition and/or shape of the biofilm streamer. As used in the invention, biofilm streamer morphology may change over time. These changes may be in the extracellular matrix, in the composition of bacteria and/or fungi in the biofilm streamer and/or in the shape of the biofilm streamer. Biofilm streamer growth would be an example of a change in biofilm streamer morphology.

In the present invention, "biofilm streamer promotion element" is defined as any feature of the local environment in a liquid flow system that, in the presence of pressure driven flow, serves as the site for biofilm streamer formation. For example, these biofilm streamer promotion elements may be roughened surfaces along the flow path, may be curves in the channel directing the fluid flow, may be a turn in the channel directing the fluid flow, may be a corner in the channel directing the fluid flow, may be an edge or mound projecting into the lumen of the channel directing the fluid flow, may be a constriction or expansion in the channel directing the fluid flow, and/or may be provided by an object placed within the channel directing the fluid flow.

In the present invention, "channel" is defined as a passage directing the flow of a fluid. As used in the invention, a channel may be an enclosed hollow tube. The cross section of the tube may be of any suitable geometry as is known by those of skill in the art. In one example the cross section is circular, oval, square, rectangular and/or irregularly shaped. The tube may have a constant cross-sectional area and/or it may be variable (e.g. it may constrict in certain areas and/or expand in others). The cross section of the channel may change shape along its length. In other examples, the channel may be a depression, gutter, groove and/or furrow. This depression may be shallow, deep, narrow and/or wide. In other examples, the channel may be provided by the gap between two parallel flat planar surfaces placed close together. In still other examples, the channel may be part of a larger device or machine. The channel may be a fluid flow conduit in an implantable medical device. The channel may also be a fluid flow conduit in machinery used in industrial processes. The channel may be very small (i.e. just large enough for fluid and bacterial or fungal cells to flow through) or very large (i.e. the large culverts and pools used in a waste water treatment facility.)

In the present invention, "lumen" is defined as the area in a channel that is designed to direct the flow of fluid. It is defined as the interior of an enclosed hollow tube. It is the depressed area in a depression, gutter, groove or furrow. And, it is the gap between the adjacent parallel plates.

In the present invention, "inlet" is defined as location along the channel wherein fluid is introduced under controlled pressure.

In the present invention, "outlet" is defined as the location along the channel wherein fluid exits the channel driven by controlled pressure.

In the present invention, "circular" as applied to channels is defined as having a generally round cross sectional shape. As used in the present invention, circular does not require a perfectly circular cross section. In another example, circular means that the length of the diameter measured anywhere along the cross section of the channel is identical to that measured at any other point (i.e. it is perfectly circular).

In the present invention, "curved channel" is defined as a channel that is not linear between the inlet and outlet. In one example, a curved channel may represent a simple arc between the inlet and outlet of the channel. In other example, a curved channel may multiple curved sections in any of the three dimensions between the inlet and outlet.

In the present invention, "turn" is defined as a portion of a channel with a defined, discrete change in direction of the fluid flow. This turn may be of any degree. In one example, the turn is a change in direction from about 210° to about 360°, more preferably from about 220° to about 350°, more preferably from about 230° to about 340°, more preferably from about 240° to about 330°. As used herein, a turn may be rounded or may be sharp. When a turn is sharp, it may result in a corner.

In the present invention, "corner" is defined as the point or area where two lines, edges, or sides of something meet. A corner may be an edge formed by a turn in the channel. A corner may also be a raised point in the lumen of the channel. For example, a pyramidal obstruction, placed in the lumen of the channel such that the base is against the surface of the channel and the tip is directed towards the center of the channel, would form a corner.

In the present invention, "edge" is defined as a line or line segment that is the intersection of two plane faces. An edge may be formed in the channel along the inside surface of a turn. An edge may also be formed by a raised surface in the lumen of the channel. For example, a raised wedge, placed in the lumen of the channel such that the base is against the surface of the channel and the raised edge of the wedge is directed towards the center of the channel, would form an edge. The edge formed by this wedge obstruction could be placed perpendicular to the fluid flow or parallel to the flow.

In the present invention, "mound" is defined as a raised area within the lumen of the channel without any appreciable corners or edges. A used herein, a mound would be a generally curved obstruction in the lumen of the channel. In one example, the mound is a raised circular bump. In another example, the mound may be formed by placing a half-cylinder (formed by cutting perpendicular to its circular faces) into the lumen of the channel such that the flat surface is placed against the surface of the channel with the circular surface faced towards the center of the channel. The cylinder may be placed such that the semicircular top and bottom are perpendicular to the fluid flow or parallel to the flow.

In the present invention, "roughened surface" is defined as an inner surface of the channel that has an irregular surface. It may be a surface that microscopically reduces to surfaces with many corners. In another example, it may a surface with distinct geometric and irregular deformities on a macroscopic level.

In the present invention, "objects" is defined as any material that may be placed within a channel and exposed to the fluid flow. In some examples, objects may include, for example, sand, gravel, granules and the like. In other examples, objects may include portions of medical devices or industrial fluid handling machinery. For example, objects may include filter support grids, filter mesh, stents, tubing or channel components for fluid handling, valves, pumps, and the like. These objects may be of any scale from miniature components of implantable medical devices to large scale fluid handling components of industrial cooling units or food processing machinery. One of skill in the art is well versed in the range of objects that may be placed in the channel for testing according to the invention.

In the present invention, "NAFION® granules" is defined as amorphous particles of fluoropolymer first discovered in the late 1960s by DuPont. In one example, the granules are of the size and shape of sand. In another embodiment, the granules may be larger, including up to the size of grains of rice. As used herein, one of ordinary skill in the art will recognize that additional fluropolymers may be employed in the invention. In further examples, Teflon AF, Teflon FEP and CYTOP may each be used in the invention (47).

In the present invention, "welded polypropylene feed spacer mesh" is defined as mesh similar to that used in industrial reverse osmosis filters (48). As used herein, this mesh may be any porous mesh used in industrial, medical, or other fluid handling applications.

In the present invention, "stent" is defined as a mesh tube inserted into a natural passage/conduit in the body to prevent localized flow constriction.

In the present invention, "bare-metal stent" is defined as type of vascular stent without a coating (as used in drug-eluting stents, for example). These stents may be made of bare stainless steel or may be made of advance alloys (cobalt chromium, for example).

In the present invention, "pipe" is defined as a generally rigid tube used to convey fluid or compressed gases. A pipe may have an inner diameter as small as 2 mm or as large as several feet. A pipe is made of glass, any number of metals, any number of plastics or other polymeric materials, or concrete. A pipe as used herein may be any that is known to one of ordinary skill in the art.

In the present invention, "cooling tower" is defined as a heat rejection device, which extracts waste heat to the atmosphere through the cooling of a water stream to a lower temperature. The type of heat rejection in a cooling tower is termed "evaporative" in that it allows a small portion of the water being cooled to evaporate into a moving air stream to provide significant cooling to the rest of that water stream.

In the present invention, "fluid" is defined as a liquid. In one example, the fluid is water, with or without the addition of other components. These additional components may include, but are not limited to nutrients and salts needed to support bacterial growth, bacteria, chemical or biochemical probes to assist with visualization of cells or extracellular components, test compounds, and compounds for selective growth of specific bacterial strains.

In the present invention, "flow" is defined as movement of the fluid along the channel in a continuous stream.

In the present invention, "flow rate" is defined as the volume of a fluid moving along the channel per unit time.

In the present invention, "Reynolds number" is defined as a dimensionless quantity used to help predict similar flow patterns in different fluid flow situations. It is defined as the ratio of inertial forces to viscous forces and thus quantifies the relative importance of these two types of forces for given flow conditions. Reynolds numbers may be used to characterize different flow regimes within a similar fluid, such as laminar or turbulent flow. When a fluid is flowing through a closed channel such as a pipe or between two flat plates, either of two types of flow may occur depending on the velocity of the fluid: laminar flow or turbulent flow. Laminar flow tends to occur at lower velocities, below a threshold at which it becomes turbulent. A Reynolds number of less than 2320 is characteristic of laminar flow in a circular tube. A Reynolds number greater than 2320 is characteristic of turbulent flow in a circular tube.

In the present invention, "laminar flow" in a long straight channel is defined as a flow regime that occurs when a fluid flows in parallel layers, with no disruption between the layers. At low velocities, the fluid tends to flow without lateral mixing, and adjacent layers slide past one another like playing cards. For flow in a long straight channel, there are no cross-currents perpendicular to the direction of flow, nor eddies or swirls of fluids. In laminar flow, the motion of the particles of the fluid is very orderly with all particles moving in straight lines parallel to the pipe walls. For flows in more complicated geometries, such as channels with bends and corners, the laminar flow is the time-independent motion for a steady pressure drop; the flow may be three-dimensional, i.e. the velocity may have all three components non-zero, but the flow remains steady (time independent) so long as the pressure drop is constant.

In the present invention, "turbulent flow" is defined as a flow regime characterized by chaotic property changes. This includes low momentum diffusion, high momentum convection, and rapid variation of pressure and velocity in space and time. In turbulent flow, unsteady vortices appear on many scales and interact with each other. Drag due to boundary layer skin friction increases. The structure and location of boundary layer separation often changes, sometimes resulting in a reduction of overall drag.

In the present invention, "shear stress" is defined as the force/area acting tangent to a surface. In a ordinary fluid such as water the shear stress is proportional to the fluid viscosity and proportional to the velocity gradient (as defined in standard textbooks).

In the present invention, "controlled pressure" is defined as pressure applied to a fluid moving through a channel such that the pressure drop along the channel is held constant. Thus, as resistance to flow in the pipe is increased, rather than continuing to apply increasing pressure to keep the flow rate constant, the flow rate is reduced such that the pressure remains constant. As used herein, a constant pressure includes pressure that varies. For example, the pressure may "pulse" at a given frequency, for example, but the average pressure will remain constant.

In the present invention, "pumping element" is defined as any mechanism to provide force to a fluid while flowing through the channel. As used herein, the pumping element must be able to regulate the pressure applied rather than the flow rate. In one example, the pumping element is gravity. In another example, the pumping element may be a syringe, a weight, and/or pump.

In the present invention, "syringe" is defined as pump that consists of a plunger that fits tightly in a tube ("barrel"). The plunger can be pulled and pushed along inside the barrel to cause fluid to flow along a channel.

In the present invention, a "weight" is defined as a body of determinate mass, as of metal, that may be used on a balance or scale for weighing objects. This weight may be used to apply a pumping force to the fluid moving through the channel. This may be done in many ways known to one of ordinary skill in the art. For example, the weight may be placed upon a plunger of a syringe in order to apply the controlled pressure. It may also be placed on top of a collapsible, sealed bag that is attached to the channel inlet through a tube. The weight again will apply controlled pressure to the bag, thus driving the flow of the fluid through the channel.

In the present invention, "pump" is defined as any device that moves fluids by mechanical action. Pumps may be classified into three major groups according to the method they use to move the fluid: direct lift, displacement, and gravity pumps. Pumps operate by some mechanism (typically reciprocating or rotary) and consume energy to perform mechanical work by moving the fluid. Pumps operate via many energy sources, including manual operation, electricity, engines, or wind power, come in many sizes, from microscopic for use in medical applications to large industrial pumps. Pumps can be classified by their method of displacement into positive displacement pumps, impulse pumps, velocity pumps, gravity pumps, steam pumps and valveless pumps. In one example, the pump is selected from screw pumps, piston pumps, plunger pumps, diaphragm pumps, and peristaltic pumps. For any pump used, a mechanism must be employed to regulate the pressure applied to the fluid, rather than to regulate the flow rate through the channel.

In the present invention, "measuring element" is defined as any mechanism that permits measurement of the flow rate of the fluid through the channel. In one example, the measuring element consists of a dish placed upon an analytical balance. The balance is connected to a computer which continually or periodically samples the change in mass of the fluid in the dish and plots this change of mass over time. Other measuring elements are known to one of ordinary skill in the art. In another example, the measuring element is selected from piston meters, oval gear meters, helical gear meters, nutating disk meters, variable area meters, turbine flow meters, paddle wheel meters, and venturi meters.

In the present invention, "effluent collecting element" is defined as any suitable container for receiving the fluid after passing through the channel. In one example, the effluent collecting element is a dish. In other embodiments, the effluent collecting element may be, for example, an expandable plastic bag, a graduated cylinder, or other container known to one of ordinary skill in the art.

In the present invention, "analytical balance" is defined as a class of balance designed to measure small mass in the sub milligram range. Single pan mechanical substitution balance maintains consistent response throughout the useful capacity is achieved by maintaining a constant load on the balance beam, thus the fulcrum, by subtracting mass on the same side of the beam to which the sample is added. Electronic analytical scales measure the force needed to counter the mass being measured rather than using actual masses. As such they must have calibration adjustments made to compensate for gravitational differences. They use an electromagnet to generate a force to counter the sample being measured and outputs the result by measuring the force needed to achieve balance. Such measurement device is called electromagnetic force restoration sensor.

In the present invention, "computer" is defined as a device capable of executing instructions for executing the method of measuring specified herein. A computer may operate as a standalone device or can be connected (e.g. networked) to other computers. In a networked deployment, the computer can operate in the capacity of a server or a client machine in a server-client network environment, cloud computing environment, or as a peer machine in a peer-to-peer (or distributed) network environment. While only a single computer is specified, the term "computer" shall also be taken to include any collection of computers that individually or jointly execute a set (or multiple sets) of instructions to perform any one or more of the methodologies discussed herein. The computer includes a processor or multiple processors (e.g., a central processing unit (CPU), a graphics processing unit (GPU), or both), and a main memory and a static memory, which communicate with each other via a bus. The computer can further include a video display unit (e.g., a liquid crystal display (LCD) or cathode ray tube (CRT)). The computer also includes at least one input device, such as an alphanumeric input device (e.g., a keyboard), a cursor control device (e.g., a mouse), a microphone, a digital camera, a video camera, and so forth. The computer also includes a disk drive unit, a signal generation device (e.g., a speaker), and a network interface device. The disk drive unit includes a computer-readable medium, which stores one or more sets of instructions and data structures (e.g., instructions) embodying or utilized by any one or more of the methodologies or functions described herein. The instructions can also reside, completely or at least partially, within the main memory and/or within the processors during execution thereof by the computer. The main memory and the processors also constitute machine-readable media. The instructions can further be transmitted or received over a network via the network interface device utilizing any one of a number of well-known transfer protocols (e.g., Hyper Text Transfer Protocol (HTTP), CAN, Serial, and Modbus). While the computer-readable medium is stated as a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying out a set of instructions for execution by the computer and that causes the computer to perform any one or more of the methodologies of the present invention, or that is capable of storing, encoding, or carrying data structures utilized by or associated with such a set of instructions. The term "computer-readable medium" shall accordingly be taken to include, but not be limited to, solid-state memories, optical and magnetic media. Such media can also include, without limitation, hard disks, floppy disks, flash memory cards, digital video disks (DVDs), random access memory (RAM), read only memory (ROM), and the like. The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software programs for implementing the present method can be written in any number of suitable programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Perl, UNIX Shell, Visual Basic, Visual Basic Script, Virtual Reality Markup Language (VRML), ColdFusion™, Lab- VIEW™, or other compilers, assemblers, interpreters, or other computer languages or platforms.

In the present invention, "substrate" is defined as surface supporting the channel through which the fluid passes. The substrate may be any suitable solid surface as is known to one of ordinary skill in the art. In one example, the substrate is a glass coverslip. In a further example the substrate can be glass, stainless steel, plastic, polymers, sand, wire mesh, bone, teeth, skin, or blood vessels. In other examples, the substrate will be a suitable support for the channel of the invention. For example, if the channel is the tubing of a fluid handling system, the internal supports of the fluid handling system would be the substrate as used herein.

In the present invention, "microscope" is defined as an instrument used to see objects that are too small for the naked eye. In one example, a microscope of the present invention is a confocal laser scanning microscope. In another example the microscope of the present invention is an epifluorescence microscope.

In the present invention, "three-inlet port" is defined as a manifold connected to the inlet of the channel so that three separate fluids maybe introduced into the channel either separately or one at a time.

In the present invention, "multilayer microfluidic gates" are defined as a series of gates created by multilayer soft lithography so that the flow of solutions into a microfluidic channel system can be independently selected from separate ports. The gates are created using the technique described by Unger et al. (2000) Monolithic micro-fabricated valves and pumps by multilayer soft lithography. Science 288 (5463): 113-116.

In the present invention, "time until clogging (T)" is defined as the time at which the fitted flow rate drops to half its initial value.

In the present invention, "duration of the clogging transition (τ)" is defined as the time period in which the fitted flow rate decreases from 76% to 27% of its initial value.

In the present invention, "test compound" is defined as any compound added to the test system for evaluation of its effect on biofilm and/or biofilm streamer formation and growth. The effect of the test compound may be to inhibit or to enhance biofilm and/or biofilm streamer growth or morphology changes. These compounds may be pharmaceutical compound, small molecules, or biological compounds. Some examples include peptides, proteins, peptidomimetics, antibodies, non-antibody specific binding molecules, such as adnectins, affibodies, avimers, anticalins, tetranectins, DARPins, mTCRs, engineered Kunitz-type inhibitors, nucleic acid aptamers and spiegelmers, peptide aptamers and cyclic and bicyclic peptides (Ruigrok et al. Biochem J. (2011) 436, 1-13; Gebauer et al., Curr Opin Chem Biol. (2009) (3):245-55.)

In the present invention, "antibody" refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. Examples of molecules which are described by the term "antibody" in this application include, but are not limited to: single chain Fvs, and fragments comprising or alternatively consisting of, either a VL or a VH domain. The term "single chain Fv" or "scFv" as used herein refers to a polypeptide comprising a VL domain of an antibody linked to a VH domain of an antibody. Antibodies of the invention include, but are not limited to, monoclonal, multispecific, human or chimeric antibodies, single chain antibodies, Fab fragments, F9ab') fragments, antiidiotypic (anti-Id) antibodies (including, e.g., anti-Idantibodies to antibodies of the invention), and epitope-binding fragments of any of the above. The immunoglobulin molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

B. Industrial Uses

The systems and methods of the invention can be used to test materials and manufacturing methods to identify those most susceptible to biofilm and/or biofilm streamer formation, growth, and morphology changes. Thus, the invention can identify those most susceptible to clogging. In one embodiment, the systems and methods of the invention may be used to test component parts or particular materials in microfluidic or other benchtop-sized assay systems. In another embodiment, the systems and methods of the invention may be used to test entire industrial fluid handling systems or other areas where water is directed along channels. These assays can guide selection of resistant materials or to highlight potential problem areas in fluid handling systems and test potential redesigns. In a further embodiment, the systems and methods of the invention can be used to screen for effectors of biofilm and/or biofilm streamer formation, growth and morphology changes. These effectors may be genes in the bacteria themselves. By screening against various mutants, the systems and methods of the invention may serve to identify additional genes that play important roles in biofilm and biofilm streamer formation, growth and morphology changes. Once identified, these genes can be targeted by traditional drug discovery techniques to identify small molecule and/or biological inhibitors. These effectors may be small molecule and/or biological compounds. By screening against these various compounds, the systems and methods of the invention may serve to identify compounds with the ability to inhibit or to enhance biofilm and/or biofilm streamer formation, growth or morphology changes. These screens may additionally be run in the presence of various antibiotics to detect effectors that enhance antibiotic inhibition.

Compounds identified this way can be used in industrial settings, either in the presence or absence of antibiotics, to inhibit biofilm production and/or to remove antibiotic resistant bacteria, such as in a hospital or other public setting. For example, the compounds of the invention can be used to remove biofilms that have grown in moist and warm environments, such as showers, water and sewage pipes, cooling or heating water systems, (e.g., cooling towers), marine engineering systems, such as, for example, pipelines of the offshore oil and gas industry. The compounds of the invention can also be used, for example, to remove and/or prevent bacterial adhesion to boat hulls, since once a biofilm of bacteria forms, it is easier for other marine organisms such as barnacles to attach. The compounds of the invention can be used to reduce, for example, the time a boat is in dry dock for refitting and repainting, thereby increasing productivity of shipping assets, and useful life of the ships. The compounds of the invention can also be used to remove biofilm production intentionally used to eliminate petroleum oil from contaminated oceans or marine systems, once the contamination is removed.

Additionally, the compound of the invention can be used to wash, rinse or swab floors and counters, such as in food preparation areas or medical facilities, as well as medical devices, including but not limited to, stents, catheters, intubation tubes, or ventilator equipment. Still further the compounds can be used as a handwash to help eliminate spread of virulent bacteria by health workers, patients and others.

Particular species of bacteria may be especially problematic. For example, Pseudomonas aeruginosa is a pathogen that can survive in a wide range of environments. The bacterium is a public health threat because it causes a variety of secondary infections in humans, where those with burn wounds, cystic fibrosis, and implanted medical devices are particularly at risk. With an outer membrane of low permeability, a multitude of efflux pumps, and various degradative enzymes to disable antibiotics, P. aeruginosa is difficult to treat. As with other common pathogenic bacteria, antibiotic-resistant strains are an increasing problem.

Blocking virulence is one of the strategies contemplated to combat these bacteria. This approach provides less selective pressure for the spread of resistant mutants and leads to drug therapies that are effective over a greater time span compared to traditional antibiotics. Rather than preventing growth or killing the bacteria, an antivirulence approach prevents the expression of virulence traits. The bacteria that have been treated and are thus benign should then be more easily cleared by the host immune system.

EXAMPLES

Example 1

Bacterial Strains and Culture Conditions

All strains are derivatives of Pseudomonas aeruginosa PA14. Overnight cultures were grown in tryptone broth (1% tryptone in H2O, refs. 25, 28) at 37° C. with shaking. The mutant strains ΔflgK (sad-36, ref. 21), ΔpilC (sad-29, ref. 21), and ΔpelA (24) were characterized previously. A ΔlasR:: aacC1 mutant (AFS20) was a gift from A. Siryaporn (Princeton University). The PA14 strain harboring PA1/04/03::gfp inserted in the intergenic region between the glmS and PA14_73160 genes is designated PA14-gfp (25) and was a gift from the Kolter Laboratory, Harvard University, Cambridge, Mass. The lac-derived promoter PA1/04/03 results in constitutive expression of gfp (51, 52). Strains carrying the PA1/04/03::mCherry construct at the identical chromosomal site were engineered by mating a pUC-mini-Tn7 (53) derived plasmid, pAS08.2E (gift from A. Siryaporn), into the chromosome. This method resulted in strains PA14-mCherry (AFS27E, gift from A. Siryaporn), ΔflgK mCherry, ΔpilC mCherry, ΔpelA mCherry, and ΔlasR mCherry.

Example 2

Microfluidic Pressure-Driven Flow Assay and Microscopy

Figure 2A:
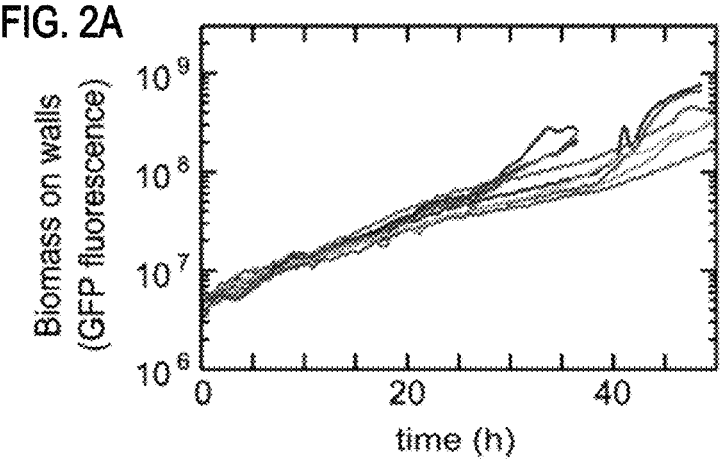
FIGS. 2A-2D show that cell growth determines time until clogging (T) while transport of cells to the biofilm streamer determines the duration of the clogging transition (τ).
Figure 2B:
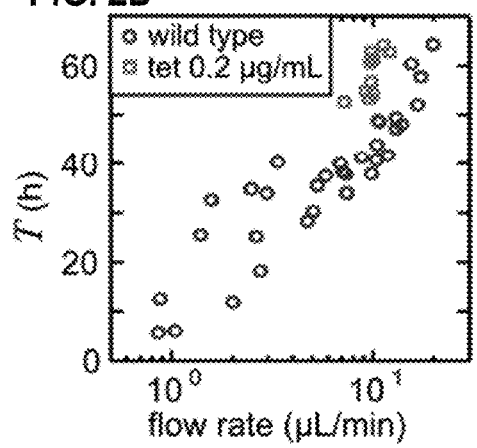
Figure 2C:
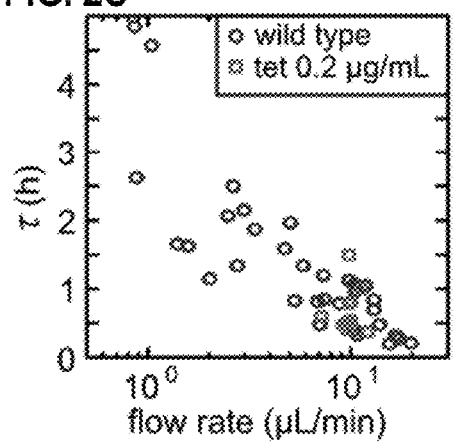
Figure 2D:
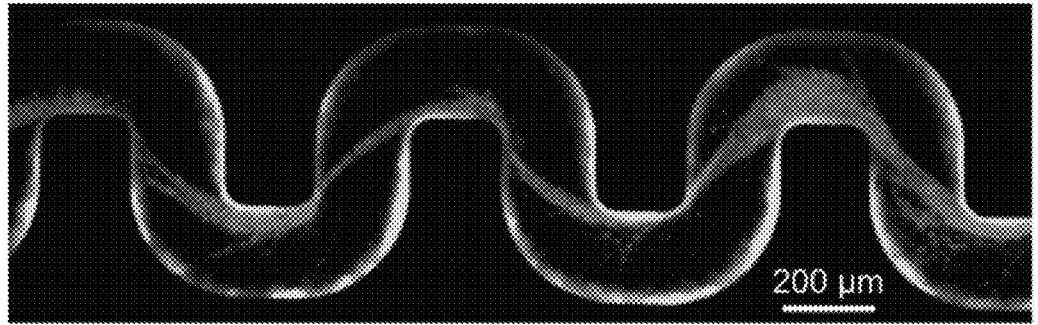
Figure 6:
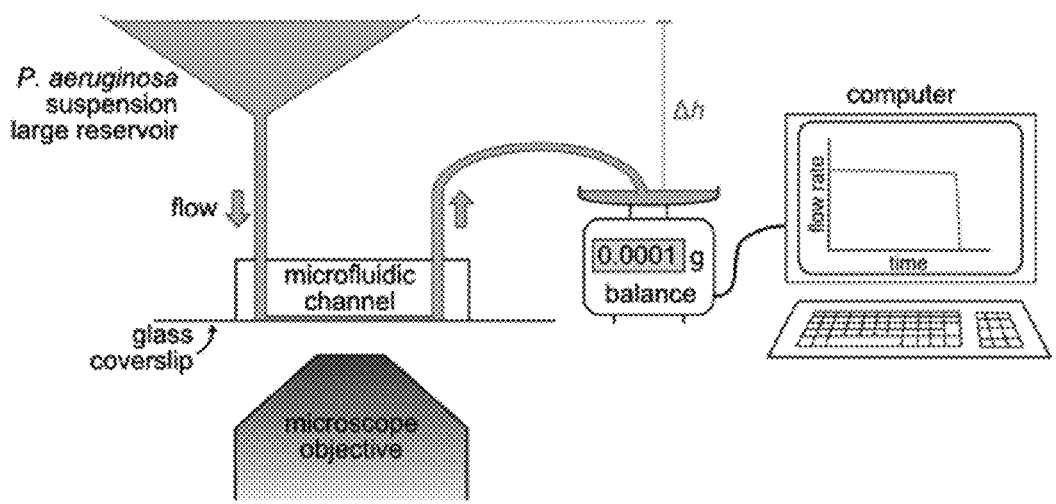
FIG. 6 shows the experimental setup of a model system of the invention. Midlogarithmic phase $P.$ $aeruginosa$ cells were loaded into a reservoir, with a large cross-sectional area at the air-water interface. The wide-bore tubing connects the microfluidic channel with the reservoir and the effluent collection dish, which is placed on an analytical balance. The height difference $\Delta h$ between the reservoir suspension and the effluent collected on the analytical balance is proportional to the applied pressure. Data of the weight of the effluent as a function of time are converted on a computer to the flow rate as a function of time. The biofilm in the microfluidic channel, filter mesh, or stent, is imaged using a confocal or epifluorescence microscope.
Figure 13A:
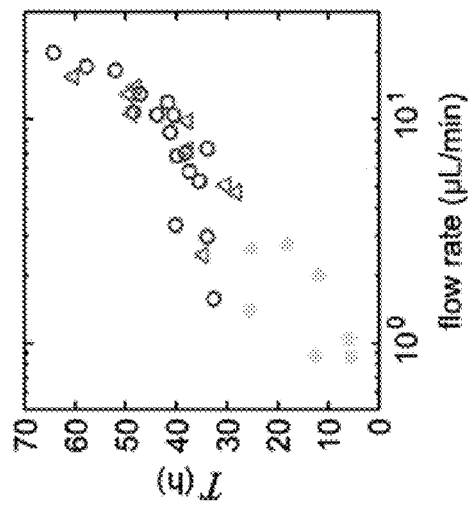
FIGS. 13A-13C show that there were no observable changes in the reservoir culture whether the culture was exchanged or not.
Figure 13B:
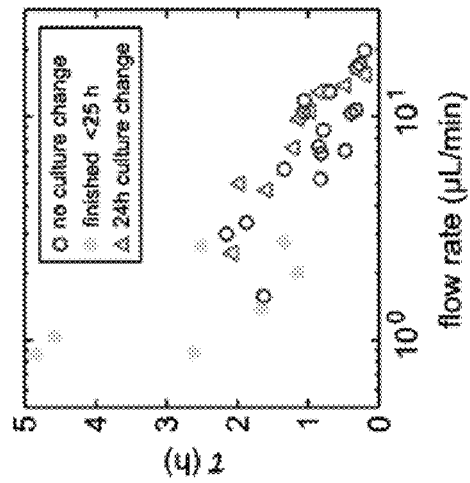
Figure 13C:
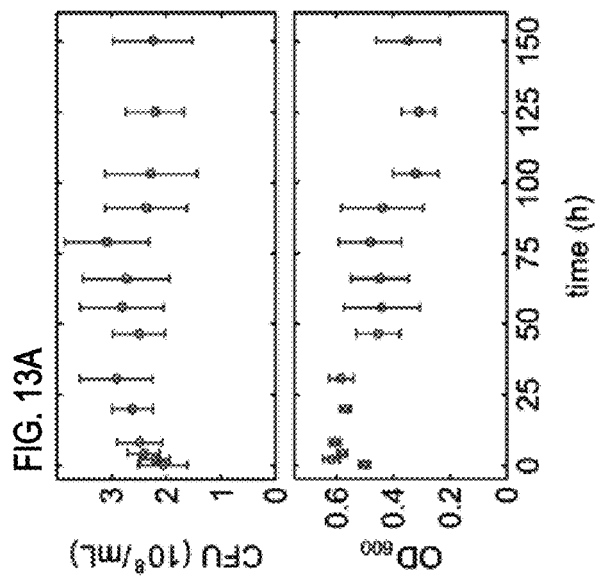

A schematic diagram of the apparatus used to investigate biofilm dynamics in a microfluidic model system is shown in FIG. 6. Overnight P. aeruginosa cultures were backdiluted 1:100 in tryptone broth and grown to midlogarithmic phase (OD600=0.5). This culture (100 mL) was used to fill a reservoir connected via Tygon tubing (inner diameter 2.4 mm) to a microfluidic channel made from polydimethylsiloxane (PDMS) (Sylgard 184, Dow Corning). The channels (FIG. 1A) are 90 µm high, 200 µm wide, and constitute the narrowest part of the experimental flow system. Analogous to the inlet, the outlet of the microfluidic channel is also connected to Tygon tubing, and the effluent culture is collected in a dish on an analytical balance. By changing the elevation of the culture reservoir above the effluent collection dish, the applied pressure difference Δp is altered, which alters the flow rate through the channel. Operating this system for 24 h with H2O at a flow rate of 15.7±0.05 µL/min reduced the liquid level in the reservoir to decrease the pressure drop across the channel by 2.1%. For experiments in which the cell concentration that is flowed through the channel is varied (FIG. 3E), we maintained the flow rate approximately constant (4.8±0.8 µL/min; ± SD between independent channels), and changed the cell concentration in the reservoir by diluting or concentrating (via centrifugation) midlogarithmic phase cells. Images of the biofilms were acquired using epifluorescence microscopy on a Nikon Ti-Eclipse microscope and a CCD camera (iXon, Andor), or a confocal laser scanning microscope (TCS SP5, Leica). Although the cfu and OD600 in the reservoir are approximately constant for more than 72 h at 22° C. (FIG. 13A), the state of the inflowing culture may change over time. Exchanging the culture in the reservoir every 24 h does not significantly change T or τ, compared with experiments in which the culture was not exchanged (FIG. 13 B and C). We thus exchanged the reservoir culture approximately every 24 h in long experiments, but used all data points shown in FIG. 13 B and C. In some experiments, the in-flowing culture was exchanged to contain a different strain (FIG. 2D and FIG. 12). These experiments were performed at a flow rate of ~18 µL/min. When the in-flowing strain was exchanged, the entire reservoir container was exchanged.

Example 3

Analysis of Flow-Rate Time Series

The weight of the effluent culture was measured every 4 s on an analytical balance (GD503, Sartorius), controlled with LabVIEW. To obtain the flow rate time series Q(t) from the effluent weight time series w(t), we computed $$Q(t) = \frac{w(t+30 \text{ s}) - w(t-30 \text{ s})}{1 \text{ min}} \frac{1}{\text{density}}, \quad \text{Eq. 1}$$

where the density was assumed to be the density of water, 1 kg/L. T and τ were calculated by fitting the function $$Q_0 / \left[1 + \exp\left(\frac{t-T}{\tau/2}\right)\right] \quad \text{Eq. 2}$$

to the measured flow rate Q(t), where Q0 is the flow rate before the clogging transition. The time τ is therefore defined as the time period in which the fitted flow rate decreases from 76% to 27% of $Q_0$, and T is the time at which the fitted flow rate is Q0/2.

Example 4

Measuring the Accumulation of Wall-Attached Biofilm

Using a flow rate of 18± 1 μL/min (±SD of n=10 independent experiments) and the PA14-gfp strain, we acquired GFP fluorescence images of the complete channel until streamers emerged. The pixel intensities at the walls were summed up to measure the wall-attached biomass.

Example 5

Staining of EPS In Situ

To visualize the different components of a streamer while it expands, we fluorescently stained the EPS produced by *P. aeruginosa* PA14-mCherry. For this assay, we used a microfluidic channel containing only 5 bends instead of the 36 bends that make up the standard channel. In addition, this channel had three inlet ports, which could be opened and closed using multilayer microfluidic gates (54). One of these inlet ports was connected to the *P. aeruginosa* PA14-mCherry culture, as in the previous assays. The second port was connected to a PBS solution, and the third port was connected to a mixture of several EPS stains dissolved in PBS. These EPS stains included 5 μM of the green fluorescent nucleic acid stain SYTO 9 (Molecular Probes) (55, 56), 20 μg/mL fluorescein isothiocyanate (FITC)-conjugated Concanavalin A (ConA), and 20 μg/mL FITC-conjugated wheat germ agglutinin (WGA). The lectin ConA (Sigma) binds to α-D-mannose, α-Dglucose, and likely alginate (56), whereas the lectin WGA (Sigma) binds to N-acetyl-D-glucosamine and N-acetylneuraminic acid (56). The nucleic acid stain was used to visualize extracellular DNA (57). High-magnification (100×) images of *P. aeruginosa* biofilms stained with SYTO 9 showed that the stain predominantly binds to extracellular, rather than intracellular, nucleic acids. To stain the EPS of the streamer before complete clogging occurred, we flowed *P. aeruginosa* PA14-mCherry cells through the channel until the streamer was rapidly expanding. Supply of the cell culture was then terminated by closing the relevant gate, and PBS was flowed through the channel to clear unattached cells. Subsequently, the PBS supply was stopped by closing the appropriate gate and the staining solution was flowed through the channel for approximately 5 min, after which the unbound stain was washed out by once again flushing the channel with PBS.

Example 6

Artificial Soil, Feed Spacer Mesh, and Stents

To manufacture a 3D porous material that is geometrically similar to soil, we used granules made from the fluoropolymer Nafion, which is transparent in water and thus allows microscopic imaging deep inside the porous material (47). Nafion granules were generated from dissolved Nafion (Ion Power). The solvent was evaporated on glass slides at room temperature and the dried Nafion was cut repeatedly to generate heterogeneous granules. Before packing the Nafion granules into a straight microfluidic channel (300 μm high, 1 mm wide), the channel was air-plasma treated. The PDMS channel was subsequently bonded to glass by a heat treatment at 95° C. for 1 min. Welded polypropylene feed spacer mesh (gap size 1.8×1.8 mm; Industrial Netting), similar to that used in industrial reverse osmosis filters (48), was placed in a rectangular PDMS channel (900 μm high, 10 mm wide), which was subsequently bonded to a glass microscope slide. A bare-metal stent (diameter 2.5 mm, length 28 mm) was placed into a nearly circular PDMS channel, which was molded onto tubing that was later withdrawn. The porous material, feed spacer, and stent were all exposed to *P. aeruginosa* PA14-gfp culture, which was flowed through the channels for approximately 12 h.

Example 7

Influence of Biofilm Streamers on the Permeability of a Channel

Figure 7A:
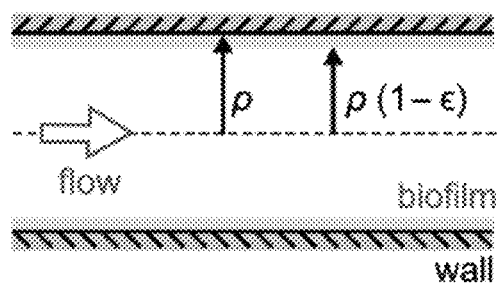
FIGS. 7A and 7B show model geometries for calculating the influence of biofilm streamers on permeability.
Figure 7B:
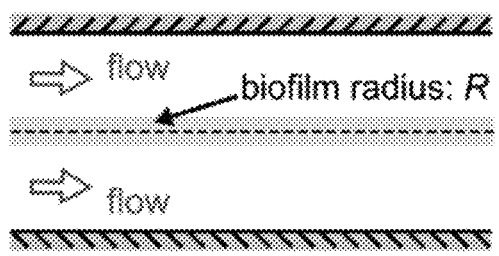

We consider two elementary cases of biomass distribution to evaluate their effect on the permeability of a channel subjected to a pressure-driven flow. In one case, the biomass forms a thin film on the surface of the channel (FIG. 7A), whereas in the second case the biomass forms a single biofilm streamer in the center of the channel (FIG. 7B). For simplicity, we model the channel as a cylindrical pipe of radius ρ.

In the case of the wall-attached biofilm, the biofilm thickness is $\epsilon\rho$, where $0 \leq \epsilon \ll 1$. For steady pressure-driven flow in a cylindrical channel, the classical Poiseuille formula relates the flow rate $Q_0$ to the total pressure drop across the whole channel per unit length $\Delta p_{tot}/L$, given by $$Q_0 = \frac{\pi \rho^4 \Delta p_{tot}}{8\eta L} \qquad \text{Eq. 3}$$

where η is the dynamic viscosity of the fluid. When biofilm accumulates as a thin film on the walls of the channel, as indicated in FIG. 7A, the flow rate is obtained by using the new radius $\rho(1-\epsilon)$. Therefore, for the identical pressure drop per unit length, the flow rate in the presence of a surface-attached biofilm $Q_{film}$ satisfies $$\frac{Q_{film}}{Q_0} = (1-\epsilon)^4 \qquad \text{Eq. 4}$$

which reduces to $Q_{film}/Q_0 \approx 1-4\epsilon$, with the assumption $\epsilon \ll 1$.

In the case of a biofilm streamer positioned in the middle of the channel, we treat the streamer as a cylinder of radius R with a no-slip boundary. We have observed that the biofilm streamer slowly moves along the flow, with a migration speed that is much lower than the flow speed. This finding justifies the assumption that the streamer provides a no-slip surface. The flow geometry thus reduces to the standard problem of a pressure-driven flow between two coaxial cylinders (1). Using cylindrical coordinates (radial coordinate r), the flow velocity along the direction of the cylinders is $$u(r) = \frac{\rho^2 \Delta p_{tot}}{4\eta L}\left(1 - \left(\frac{r}{\rho}\right)^2 - \left[1 - \left(\frac{R}{\rho}\right)^2\right]\frac{\ln(r/\rho)}{\ln(R/\rho)}\right) \qquad \text{Eq. 5}$$

This velocity field can be integrated over the annular cross-section of the concentric cylinders to yield the flow rate in the presence of a streamer Qstreamer, which is given by $$\frac{Q_{streamer}}{Q_0} = \frac{\left(\frac{R}{\rho}\right)^4 [1 - \ln(R/\rho)] + 1 + \ln(R/\rho) - 2\left(\frac{R}{\rho}\right)^2}{\ln(R/\rho)} \quad \text{Eq. 6}$$

To compare the flow rate reduction caused by the wall-attached biofilm with the flow-rate reduction caused by the streamer, we fix the streamer radius R such that the biomass in the streamer is equal to the biomass in the wall-attached biofilm. Due to cylindrical symmetry, $2\pi\rho^2\epsilon = \pi R^2$, which can be rearranged to give $R = \rho(2\epsilon)^{1/2}$. For small biofilms, $\epsilon = 0.01 \ll 1$, we find $$\frac{Q_{film}}{Q_0} = 1 - 4\varepsilon = 0.96 \quad \text{Eq. 7}$$

$$\frac{Q_{streamer}}{Q_0} = 1 + \frac{2}{\ln\varepsilon} = 0.51 \quad \text{Eq. 8}$$

Thus, a thin, wall-attached biofilm on the surface of the channel leads to a reduction in flow rate of a few percent, whereas the same biomass bound in a biofilm streamer along the centerline of the channel reduces the flow rate by ~50%.

Example 8

Growth of a Solid Biofilm Streamer

We consider a solid biofilm streamer with its axis oriented transverse to the flow direction, as in FIG. 3A. This orientation is motivated by FIG. 8, which shows that the streamers in our microfluidic system are partially transverse to the flow direction. We assume that the streamer radius R is much smaller than the channel diameter so that we can neglect the presence of the confinement and treat the streamer as a solid cylinder in an unbounded flow. We further assume that the streamer is very long so that the flow is essentially 2D and only varies in the plane that is orthogonal to the streamer axis.

For the low Reynolds numbers (Re) considered in our experiments, the flow around the streamer is laminar (Re=0.1-2 for different flow rates). Cells that are carried by the flow can move across streamlines by the intrinsic diffusion of their cell body as well as their self-generated motility, which leads to an effective diffusion constant D. Diffusion across streamlines in the vicinity of the streamer can cause a cell to come in contact with the streamer, in which case we assume that there is a probability a that the streamer absorbs the cell. If the cell is absorbed by the streamer, the streamer expands its cross-sectional area by an area A. The growth rate of the cross-sectional area of the streamer is therefore given by $$2\pi R \frac{dR}{dt} = \alpha I A \quad \text{Eq. 9}$$

where I is the number of cells per unit length of the streamer that come in contact with the streamer per unit time, and t is time. As cells are constantly absorbed by the streamer, the cell concentration c is expected to change close to the streamer, which, by Fick's law, causes a flux of cells $-D\nabla c$. This flux can be integrated over the cross-sectional area of the streamer S to obtain $$I = -D \int \left[\frac{\partial c}{\partial r}\right]_{r=R} dS \quad \text{Eq. 10}$$

$$I = DC \, Nu, \quad \text{Eq. 11}$$

where C is the cell concentration in the bulk far away from the streamer, and Nu is the mass transfer Nusselt number (also known as the Sherwood number). As we expect the growth rate of the streamer dR/dt to be much smaller than the average flow speed V, the Nusselt number is governed by the time-independent advection-diffusion equation $$D\nabla^2 c = (u \cdot \nabla) c, \quad \text{Eq. 12}$$

where u is the flow field around the streamer. The solution for u was obtained by Tomotika and Aoi (2). Using this solution for u, Friedlander (3) solved Eq. 12 for c and showed theoretically that $$Nu \cong \left(\frac{VR}{D(2 - \log Re)}\right)^{1/3} \quad \text{Eq. 13}$$

This result for Nu was confirmed experimentally for our values of the Reynolds number (4). Using Re≈1, we obtain $$I \approx 0.8 \, C(D^2 RV)^{1/3}. \quad \text{Eq. 14}$$

To solve Eq. 9 for R(t), we need to obtain an expression of Eq. 14 in terms of R, which reduces to finding an expression for V in terms of R. Experimental studies on cylinders oriented transverse to the flow direction have shown that the drag force on the cylinder per unit length F obeys $$F \approx 7\eta V \quad \text{Eq. 15}$$

for our values of the Reynolds number (5), which is consistent with theoretical results for F that are based on the solution for u (2). For an unbounded flow, the pressure difference Δp that drives the flow is equal to the pressure drop across the streamer. The streamer initiates across one turn of the model microfluidic channel and the pressure difference that drives the flow for such a section of the channel is $\Delta p \approx \Delta p_{tot}/35$ (see FIG. 1A for an image of the channel, which has about 35 turns). As the pressure drop across the streamer occurs over a length scale R, the drag per unit length due to Δp is $$F \approx E \, R \, \Delta p \quad \text{Eq. 16}$$

where $E = O(1) \sim 1$, analogous to the expression for the drag on a sphere. Combining our equations for F, we obtain $$V \approx \frac{R\Delta p}{7\eta} \quad \text{Eq. 17}$$

This expression for V is a peculiarity of 2D fluid mechanics, but can be substituted into Eq. 14 to obtain $I \approx 0.4 \, C(\Delta\rho D^2 R^2/\eta)^{1/3}$. This function for I can then be used to rearrange Eq. 9, yielding $$\frac{dR}{dt} = BR^{-1/3} \quad \text{Eq. 18}$$

where the constant is $B \approx 0.07 \alpha CA(D^2 \Delta \rho/\eta)^{1/3}$. This equation for dR/dt can be solved easily to obtain $$R(t) \approx \left(\frac{4}{3}Bt + \text{const}\right)^{3/4} \qquad \text{Eq. 19}$$

Figure 10B:
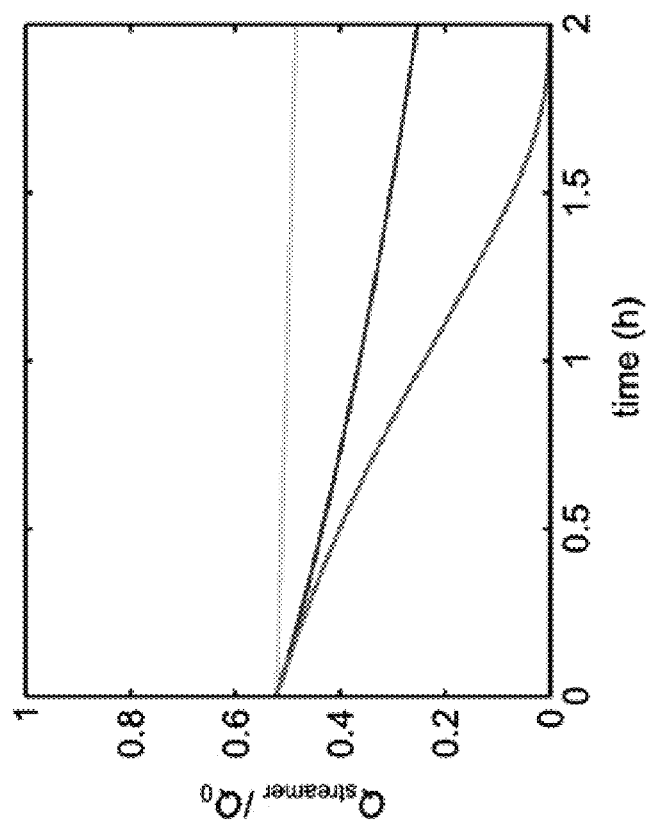
FIGS. 10A and 10B show model results for dynamics of streamer growth and flow rate decrease. The model for streamer growth based on a porous streamer predicts the red lines in FIG. 10A and 10B, assuming $\tau_{theory}$=1 h. The model based on an advection-diffusion process predicts the blue lines (for $\alpha$=1) and the green lines (for $\alpha$=0.1). Using the parameter $\alpha$=1 leads to an upper bound on the streamer growth rate, as it implies that 100% of the cells that come in contact with the streamer are absorbed by it. Both models assume an initial condition of R(t=0)=10 µm. To estimate a conversion of the results for R(t) into the flow rate $Q_{streamer}$, we used Eq. S4, which was derived for a streamer that is coaxial with a channel of circular cross-section, for which we assume a radius ρ=75 µm. Both models make strong simplifying assumptions, yet the model based on a porous streamer yields results that more closely resemble the experimental dynamics.

Based on our expression for B and Eq. 3 we can estimate the magnitude of B. Using our experimental parameters $C=2\times10^{-4}$ cells/$\mu m^3$, $A=2$ $\mu m^3$, $\rho=75$ $\mu m$, $Q_0=10^{-9}$ $m^3$/min, $L=2\times10^{-2}$ m, $D=10^{-10}$ $m^2$/s, and $\Delta\rho \approx \Delta\rho_{tot}/35$, we obtain $B \approx \alpha$ 20 $\mu m^{4/3}$/h. To understand the meaning of this value for B, we can complete the solution for R(t) by fixing the integration constant in Eq. 19 by setting R(t=0)=10 $\mu m$ (motivated by FIG. 8). The dynamics of R(t) for this condition are plotted in FIG. 10A for the upper bound $\alpha=1$ (blue line) and $\alpha=0.1$ (green line), which assumes that 100% or 10% of the cells that come in contact with the streamer are absorbed, respectively. To translate the dynamics of R(t) into the dynamics of the flow rate Q(t), we note that FIG. 8 shows that the streamer is oriented partly transverse and partly along the flow direction. We can therefore get a rough estimate of Q(t) by using Eq. 6, which was derived for a streamer that is coaxial with a channel of circular cross-section. The resulting Q(t) is plotted for $\alpha=1$ and $\alpha=0.1$ in FIG. 10B.

FIG. 10 shows that R(t) and Q(t) predicted by this model change too slowly to fully account for the rapid clogging transitions we observe experimentally. Although growth of streamers by the advection-diffusion process discussed in this section is likely to take place, the majority of the streamer growth is likely to be due to other mechanisms.

Example 9

Growth of a Porous Biofilm Streamer

As in the discussion of the growth rate of a solid streamer above, we assume that the porous streamer is oriented transverse to the flow direction (motivated by FIG. 8) and that the streamer is very long so that the flow field only varies in the plane that is orthogonal to the streamer axis. The streamer is now assumed to be porous so that liquid and cells can flow through it, yet we still assume that the streamer radius is much smaller than the channel diameter so that we can neglect the effects of the channel walls.

If a cell that is caught by the streamer adds an area A to the cross-sectional area of the streamer, the rate of expansion of the streamer cross-section is given by $$2\pi R = \frac{dR}{dt} = \beta IA \qquad \text{Eq. 20}$$

analogous to Eq. 9 for the solid streamer. However, now I is the number of cells per unit length of the streamer that flow through the streamer per unit time, and $\beta$ is the fraction of these cells that get caught in the streamer. For simplicity, we calculate an upper bound on the streamer growth rate by assuming that the streamer is entirely transparent, i.e., cells flow through it at the same speed as if there was no streamer present. This means that there is a flux of cells J=CV through the porous streamer, which results in $$I = J \cdot 2R. \qquad \text{Eq. 21}$$

To solve the above differential equation for R(t), we again use Eq. 17 to obtain $I \approx 2C\Delta\rho R^2/\eta$, which we substitute into Eq. 20 to obtain $$\frac{dR}{dt} \approx \frac{\beta AC\Delta p}{7\pi\eta}R \qquad \text{Eq. 22}$$

which can be solved to give $$R(t) \propto \exp\left(\frac{t}{\tau_{theory}}\right) \qquad \text{Eq. 23}$$

$$\tau_{theory} \approx \frac{7\pi\eta}{\beta AC\Delta p} \qquad \text{Eq. 24}$$

We further note that $\Delta p$ is proportional to the flow rate before the appearance of the streamer $Q_0$ (Eq. 3). The flow rate $Q_0$, in turn, is simply the average flow speed in the channel before the appearance of the streamer U multiplied by the cross-sectional area of the channel. The timescale of the exponential growth of the streamer can therefore be rewritten as $$\tau_{theory} \propto \frac{1}{CU} \qquad \text{Eq. 25}$$

The dependence $\tau_{theory} \propto C^{-1}$ results from the assumption that the flux of cells that become caught in the streamer is simply proportional to the flux of cells that flow through the streamer, i.e., I=2RVC. We have determined that only a very small fraction of the cells actually gets caught. However, assuming that only 1% of the cells flowing through the streamer get caught (by setting $\beta=0.01$) will not change the final functional dependence of $\tau_{theory}$ on C, except for a numerical prefactor. To obtain a relation that is closer to the experimental result $\tau \propto C^{-0.6}$, the number of cells that get caught must depend on the cell density. Such cell-density-dependent effects are plausible as 6-10% of the *Pseudomonas aeruginosa* genome is regulated by quorum sensing (6, 7), which may include genes responsible for adhesion to an existing biofilm.

We can estimate the magnitude of $\tau_{theory}$ using Eqs. 24 and 3, and our experimental parameters $C=2\times10^{-4}$ cells/$\mu m^3$, $A=2$ $\mu m^3$, $\rho=75$ $\mu m$, $Q_0=10^{-9}$ $m^3$/min, and $L=2\times10^{-2}$ m. Bearing in mind that we derived an upper bound on the streamer growth rate in this model (see the comment above Eq. 21), which yields a lower bound on $\tau_{theory}$, we can use these parameter values to obtain $\tau_{theory} \sim 0.02/\beta$ h. Although the exact value of $\beta$ is unclear, we have determined that only a very small fraction of the cells gets caught in the streamer, and values of $\beta \sim 10^{-2}$ appear plausible, which yield values for $\tau_{theory}$ that are on the same order of magnitude as experimentally observed clogging timescales $\tau$ (FIG. 3).

Figure 10A:
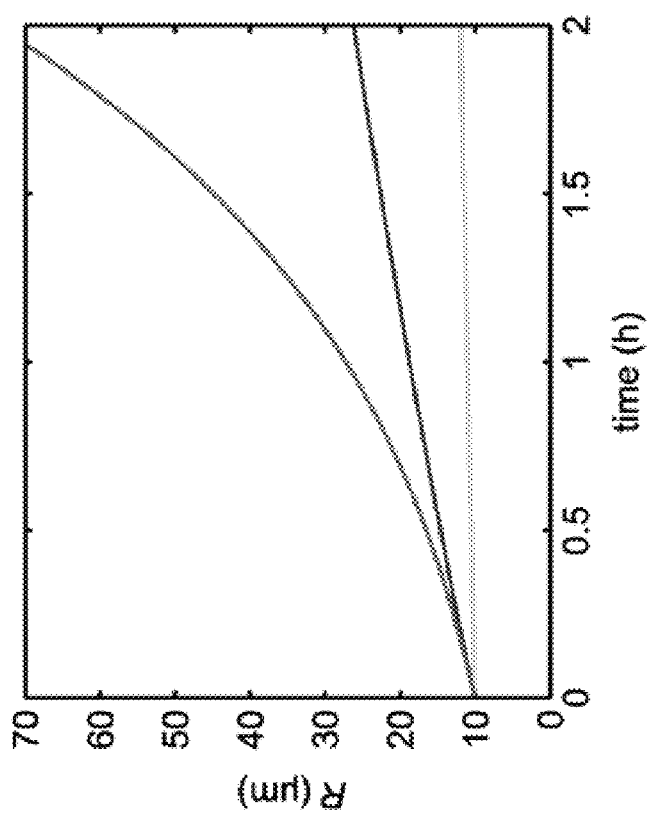

FIG. 10A shows R(t) for a porous streamer (Eq. 23) using R(t=0)=10 $\mu m$ as an initial condition. Both models make strong simplifying assumptions, yet FIG. 10 shows that the model based on a porous streamer predicts a faster increase in R, which leads to a faster decrease of Q, compared with the model that describes streamer growth as an advection-diffusion process.

Example 10

Figure 1B:
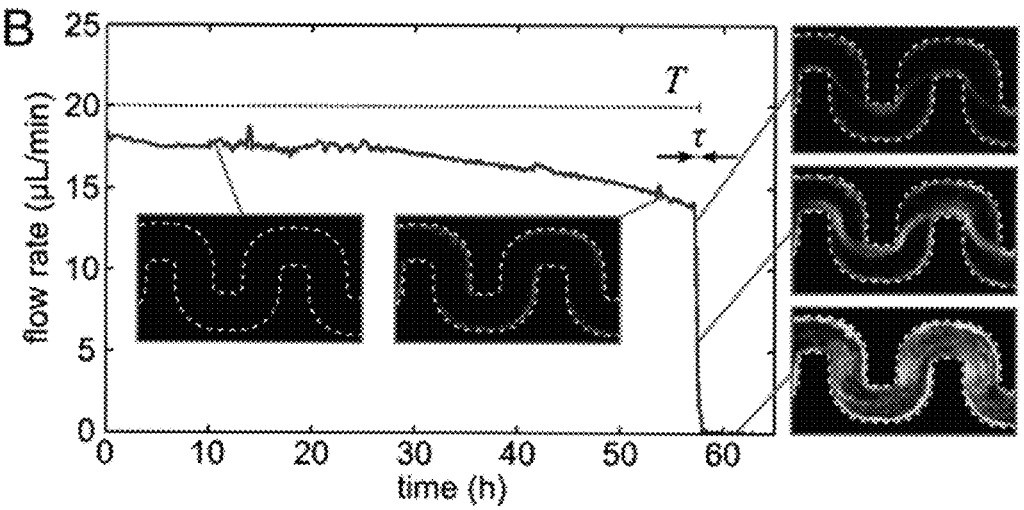

Biofilm Streamer Growth and Not Biofilm Growth Dramatically Affects Flow Rate in Model System Using our model microfluidic flow system (FIG. 1A, FIG. 6), we discovered that biofilm growth on the walls of the chamber, which has been the focus of much previous work (26, 27), only modestly affects the flow rate through this channel over a period of T≈50 h. By contrast, biofilm streamers that initiate on corners (25, 28, 29) rapidly expand and cause a catastrophic disruption of the flow on timescales as short as τ≈30 min (FIG. 1B) in our model channels, which are 200 μm wide and 90 μm high. A streamer causes a dramatic decrease in flow rate, even in a 3D environment where the flow can pass above and below the streamer, because it consists of immotile biomass, suspended in the center of the channel where the flow speed would be highest in the absence of a streamer. A model calculation (FIG. 7) confirms that for flow driven by a constant pressure, a biofilm growing on the walls of the channel has a significantly weaker effect on flow than the same volume of biofilm positioned in the center of the channel. However, such arguments cannot explain why the time until clogging T is long, whereas the duration of the clogging transition τ is short.

The exponential accumulation of cells on the walls of the channels (FIG. 2A) indicates that the accumulation process is dominated by growth (doubling time 6.5±1 h) rather than attachment of cells that are flowing by, because attachment would result in a subexponential accumulation rate. For example, a constant attachment probability for each cell per unit time would only yield a linear accumulation of wall-attached biomass with time, to first approximation. However, cells must be able to attach to the walls as the channel is initially seeded with sterile medium. We observed that flow shears off streamers from the biofilm positioned at the corners (FIG. 8). These streamers initially consist primarily of extracellular polymeric substances (EPS; refs. 4, 5) and over time, these filaments bridge the distances between corners and capture cells flowing by. Flow therefore affects the biofilm structure not just by providing nutrients (14, 15) but also by actively shaping the biofilm (30, 29, 25).

Figure 9:
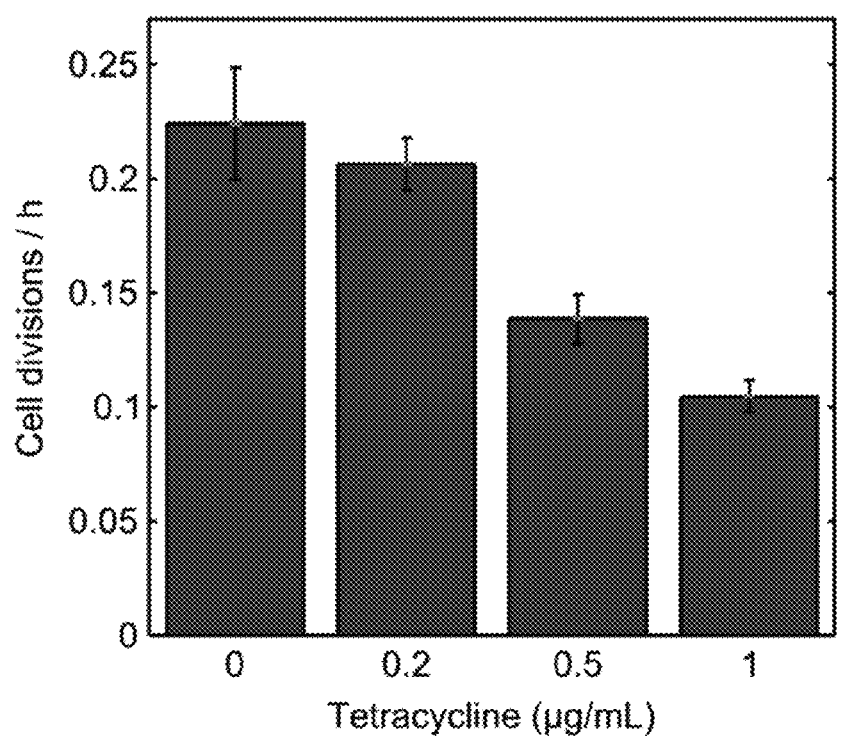
FIG. 9 shows the growth rate changes due to tetracycline. $P.$ $aeruginosa$ was grown at 22° C. in 96-well plates without shaking. By acquiring OD600 measurements every 20 min, growth curves were obtained from which we extracted the maximum growth rate for each well. Black error bars correspond to the SD of the growth rate observed in n=32 different wells for each concentration of tetracycline, and red error bars correspond to the SEM. The minimum inhibitory concentration of tetracycline for $P.$ $aeruginosa$ is 32 µg/mL (Jayaraman P, et al. (2010) Activity and interactions of antibiotic and phytochemical combinations against $Pseudomonas$ $aeruginosa$ in vitro. Int J Biol Sci 6(6):556-568; Tote K, et al. (2009) Inhibitory efficacy of various antibiotics on matrix and viable mass of $Staphylococcus$ $aureus$ and $Pseudomonas$ $aeruginosa$ biofilms. Int J Antimicrob Agents 33(6): 525-531.)

Because the wall-attached biofilm is a necessary precondition for streamer formation, slowing growth should delay clogging. Indeed, we found that T is prolonged by the addition of low levels of tetracycline, a bacteriostatic compound (FIG. 2B; see FIG. 9 for the effect on growth rate), which indicates that T is determined by cell growth.

Example 11

Biofilm Streamers Act as a Porous, Sieve-Like Mesh to Capture Cells and EPS

As τ is independent of growth (FIG. 2C), some other mechanism must be responsible for the clogging duration. We wondered whether advective transport of cells to the clogging site could be responsible for τ. To test this idea, we loaded the apparatus with cells expressing gfp for the first 43 h, a time that is significantly before the clogging transition is expected. At this time, we exchanged the in-flowing culture to one that exclusively contains cells that express mCherry rather than gfp, but are otherwise isogenic. We discovered (FIG. 2D) that streamers contain only mCherry expressing cells, while only very few mCherry expressing cells attached to the resident (green) biofilm on the walls of the channel. The rapid clogging transition is therefore due to cells that are transported to the clog-forming streamers.

To determine how cells that are transported by flow can cause rapid clogging, we developed quantitative models of streamer growth. Although many theories of biofilm buildup in porous materials have been proposed previously (26, 27, 31-33), they do not apply to our case, as biofilm streamers were not included in these theories, and we have now demonstrated that they are of crucial importance in nonuniform flow systems. Consider first the case of a solid streamer (FIG. 3A). Cells constantly flow past this streamer, and some of them migrate across streamlines and come in contact with the streamer, in which case we assume there is a probability a that the cells get absorbed. For the parameters of our experiments, this advection-diffusion process predicts (SI Text) that the radius R of such a streamer would grow approximately as R~11 μm $(\alpha t)^{3/4}$, as a function of time t in hours. Such streamer growth dynamics and the resulting flow rate decrease are slow (FIG. 10) and are therefore unlikely to be the dominant contribution to the experimentally observed rapid clogging. However, if we assume that the biofilm streamer behaves like a permeable, porous material (27, 31), with cells flowing through it (FIG. 3B), the equations for the streamer growth predict that the streamer grows exponentially fast, $R \propto \exp(t/\tau_{theory})$, with a growth timescale $\tau_{theory}$ that is of a similar magnitude to the experimentally observed clogging time scales. FIG. 10 shows that the dynamics predicted by the model based on a porous streamer are qualitatively more consistent with the experiments than the results from an advection-diffusion-based model of a solid streamer. High-resolution confocal images of the biofilm structure during streamer growth reveal (FIG. 3C) that the assumption of a porous streamer is indeed justified: the main streamer is a network of smaller biofilm filaments with numerous gaps that create a sieve-like mesh that catches cells, and possibly EPS, flowing through it (FIG. 8).

Our model of streamer growth, based on a permeable streamer, can be further tested by noting that this model predicts a functional dependence of the clogging time scale $\tau_{theory} \propto U^{-1} C^{-1}$, where U is the average flow speed prior to the emergence of streamers, and C is the density of cells in the medium that flows past the streamer (the full expression for $\tau_{theory}$ is given above). FIG. 3D shows that $\tau \propto U^{-0.98}$, consistent with the prediction for a porous streamer. In addition, $\tau \propto C^{-0.6}$ (FIG. 3E) at a fixed flow rate of 4.8±0.8 μL/min, which is a weaker functional dependence of τ on C than the model predicts. This discrepancy likely arises because $\tau_{theory} \propto C^{-1}$ results from the assumption that there is a fixed probability that a cell that flows through the streamer is caught by the streamer, independent of C. This basic physical model does not include biological effects on streamer formation, such as the contributions of particular genes, and their cell-density-dependent regulation (34, 35).

Example 12

Figure 11:
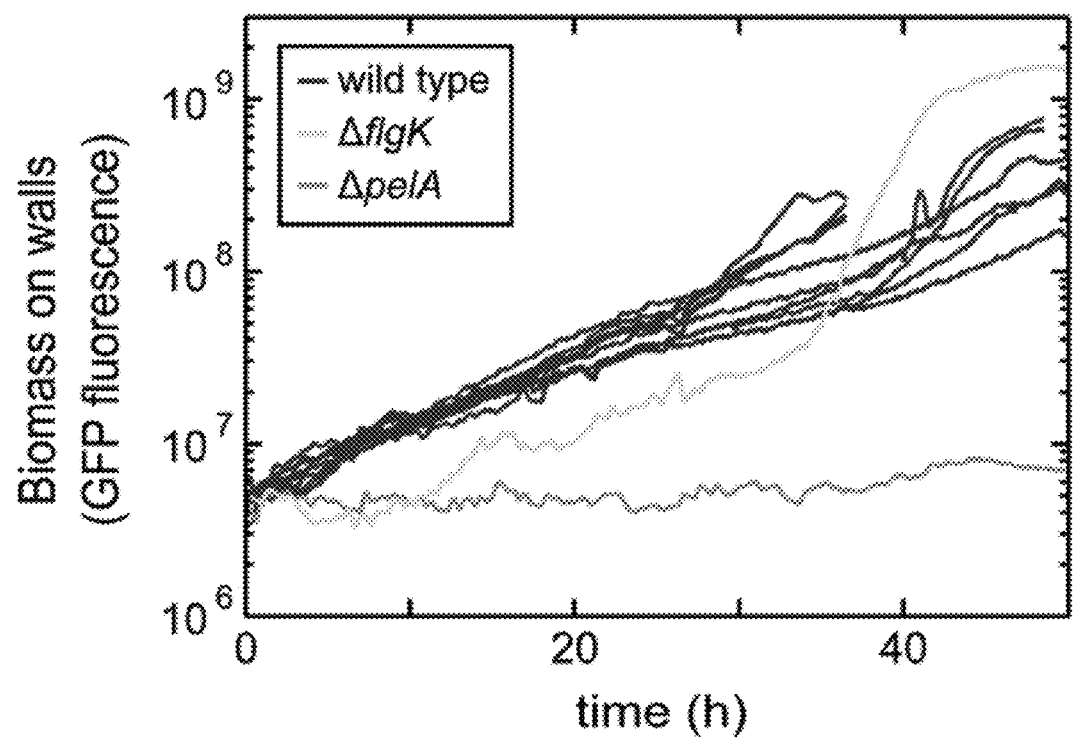
FIG. 11 shows the biomass increase for the ΔflgK and ΔpelA strains compared with the wild type. The flagella mutant strain displays a delay in biomass accumulation for the first ~10 h, but then increases in biomass with a doubling time comparable to the wild type. After ~35 h, the ΔflgK strain develops a streamer, which leads to a rapid increase in biomass. Over the same time the ΔpelA strain does not develop a significant amount of biomass.
Figure 12B:
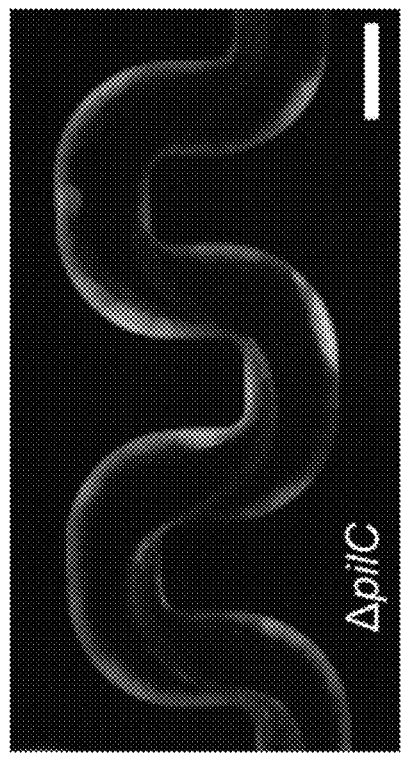
FIGS. 12A-12D show that mutants get caught in wild-type EPS. For the first 43 h, PA14-gfp is flowed through the channel, and cells build a wall-attached biofilm. The inflowing culture is then exchanged to only contain cells expressing mCherry. The GFP and mCherry color intensity is scaled between the minimum and maximum pixel intensity in each channel.
Figure 12D:
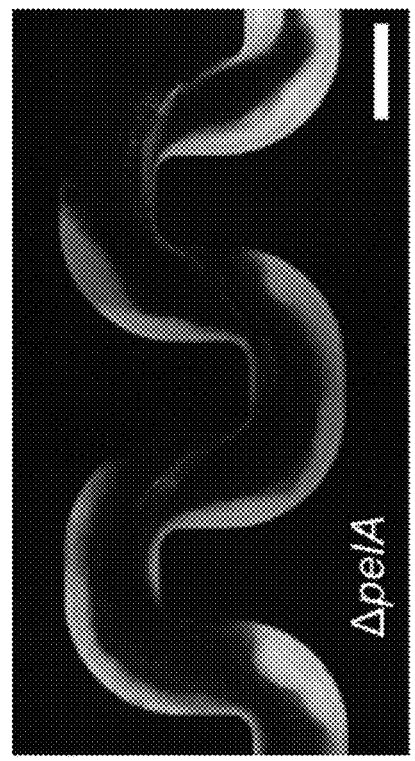
Figure 12A:
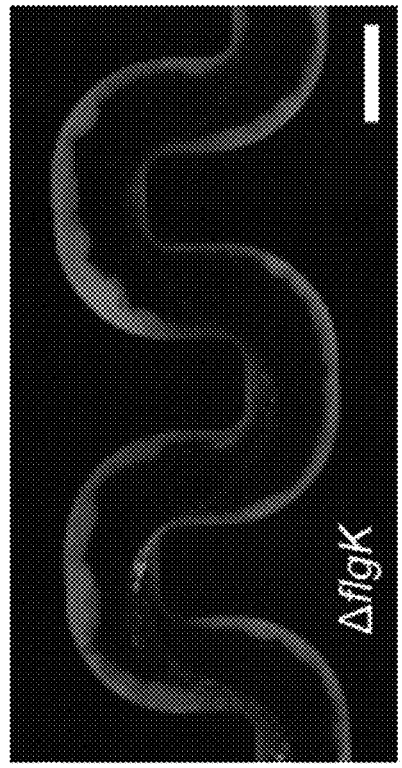
Figure 12C:
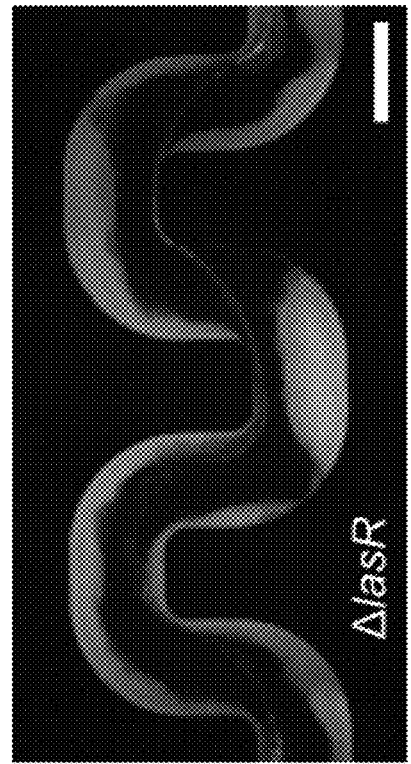

Effect of Gene Mutations on Biofilm Growth, Biofilm Streamer Growth, and Clogging Transition A general question applicable to all microbiological studies of gene regulation is whether the genes that are crucial for a particular phenotype under laboratory conditions are also crucial in natural environments, where organisms often encounter different nutrient sources, surface chemistries, and physical environments. Our system, which is designed to mimic physical aspects of realistic habitats, allows us to compare the biofilm morphology (FIG. 4 C-F) and clogging dynamics (FIG. 4 A and B) of wild type and mutant strains harboring defects in genes required for biofilm formation on smooth surfaces. In standard assays with glucose-based medium, flagellar-mediated swimming motility leads to increased residence times of cells near surfaces (36), and flagella also enhance attachment to surfaces (21, 22, 37). However, we find that a nonmotile flagellar mutant (ΔflgK) forms streamers with a similar T to wild type, even though it has a significantly larger τ (FIG. 4) and it displays a delay in biomass accumulation (FIG. 11). This result suggests that swimming is not required for transport under our experimental conditions because flow provides the necessary transport of cells to the clog-forming biofilm. The delay in biomass buildup on the walls of the channel and the prolonged τ of the ΔflgK strain relative to the wild type support the hypothesis that flagella are important, but not essential, for attaching to surfaces (21, 22, 38), including biofilm streamers. Whether the longer τ is due to a lack of motility, the flagellum, or the decreased effective size of a ΔflgK cell remains unknown.

Figure 4A:
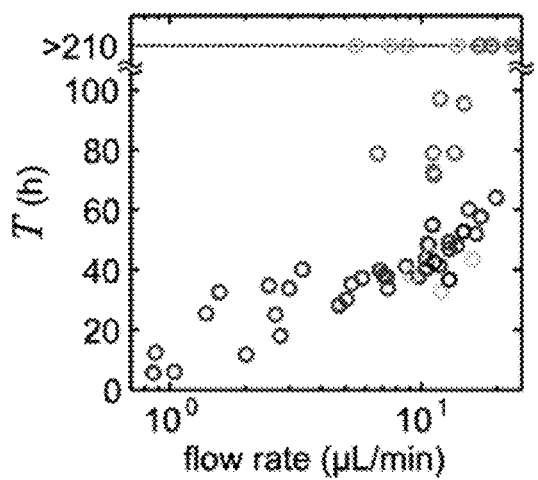
FIGS. 4A-4F show that mutant genes affect biofilm formation in nonuniform environments.
Figure 4B:
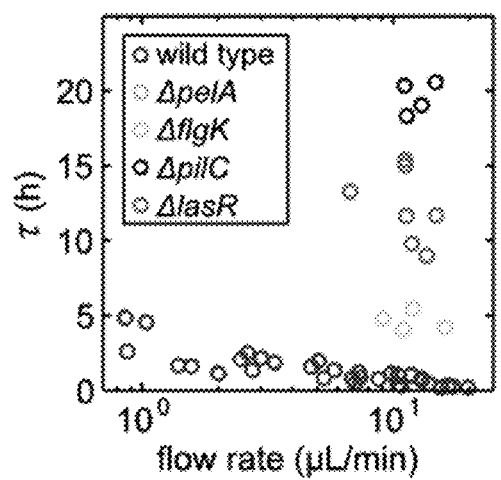
Figure 4C:
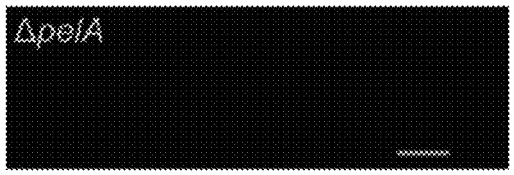
Figure 4D:
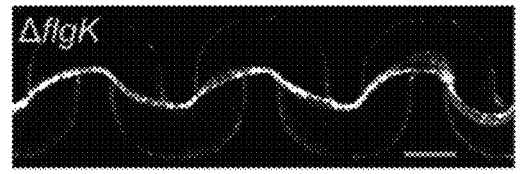
Figure 4E:
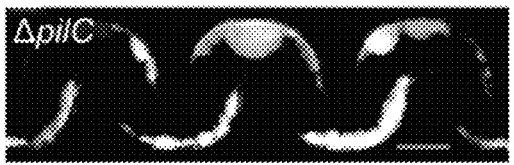
Figure 4F:
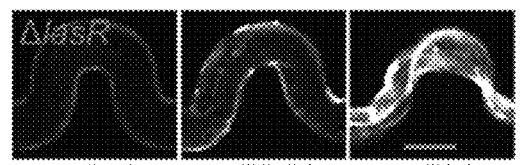

Other previously identified genes that are important for biofilm formation (4, 20-24) do have large effects in our model system. EPS production is required, as a mutant that is deficient in EPS production (ΔpelA) is unable to initiate biofilms and clog the channel (FIG. 4 A and C). Cells lacking type IV pili (ΔpilC) can form biofilms in the presence of flow (38, 39) but do not form streamers, and instead clog channels by forming thick biofilms on the walls (FIG. 4E). If, however, EPS or type IV pili mutants are flowed through a channel that contains a biofilm of wild-type cells on the walls, these mutants can participate in streamer formation (FIG. 12). This observation further supports the idea that the resident biofilm on the walls is required to generate the sieve of EPS that catches cells flowing by. Previous work showing that type IV pili are required for dynamic rearrangement of cells in biofilms (38, 39) may explain why wall-attached biofilms of the ΔpilC mutant cannot form streamers. The lasI-lasR quorum-sensing system activates the pelA gene encoding an enzyme required to make the EPS matrix (40). Thus, mutants lacking lasR are strongly impaired in biofilm development, and they produce frail biofilms consisting of cells that are less tightly bound to one another than wild-type cells (23, 40). In our system, mutants defective for quorum sensing (ΔlasR) display severely delayed clogging or no clogging, and have a dramatically different biofilm morphology than the wild type. Biofilms of the ΔlasR mutant grow on the walls of the channel, and undergo several cycles of wall detachment and deformation before complete clogging. Over time, the quorum-sensing mutant can clog the channel; however, this occurs without the formation of streamers (FIG. 4 A, B, and F), perhaps due to the reduced cell-cell cohesiveness (23, 40).

Example 13

Biofilm Streamer Formation in Other Model Systems

Figure 5A:
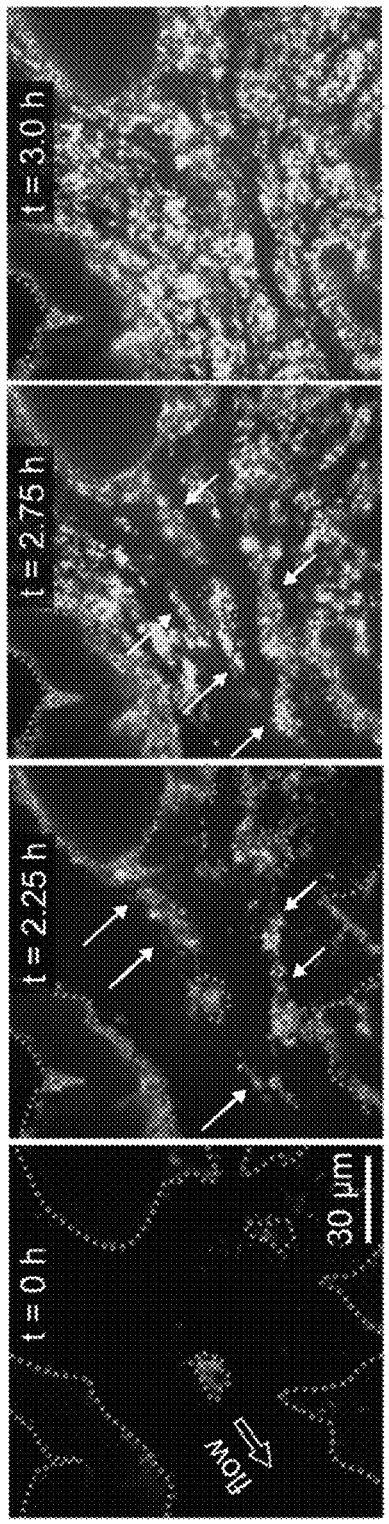
FIGS. 5A-5C show that biofilm streamers form in diverse environments.

Our results suggest that biofilm streamer formation could be critical in natural settings as streamers can cause rapid and sudden clogging. To examine whether these processes are general phenomena that are independent of our model system, we investigated biofilm morphologies in flow systems in which biofilm-induced clogging is well-documented but a mechanistic understanding is lacking. Soil is a major habitat for bacteria, including *P. aeruginosa* (16, 41). Clogging of soil-like porous materials is a primary concern in waste-water treatment reactors (6) and has been studied extensively (26, 27, 31, 32, 42-46). Direct observations of biofilm dynamics inside soil have not been possible because these environments are generally opaque beyond the first layer of granules. To overcome this limitation, we used a recently developed method to generate a transparent porous material with geometric features similar to multiple layers of fine sand (47), and observed that biofilm streamers are ubiquitous (FIG. 5A), consistent with observations in the first layer of granules in packed-bead experiments (43). We further found that in soil-like environments, biofilm streamers precede rapid clogging events of the 3D pores (FIG. 5A). Whether streamers are involved in the clogging of smaller pores in this artificial soil could not be resolved.

Figure 5C:
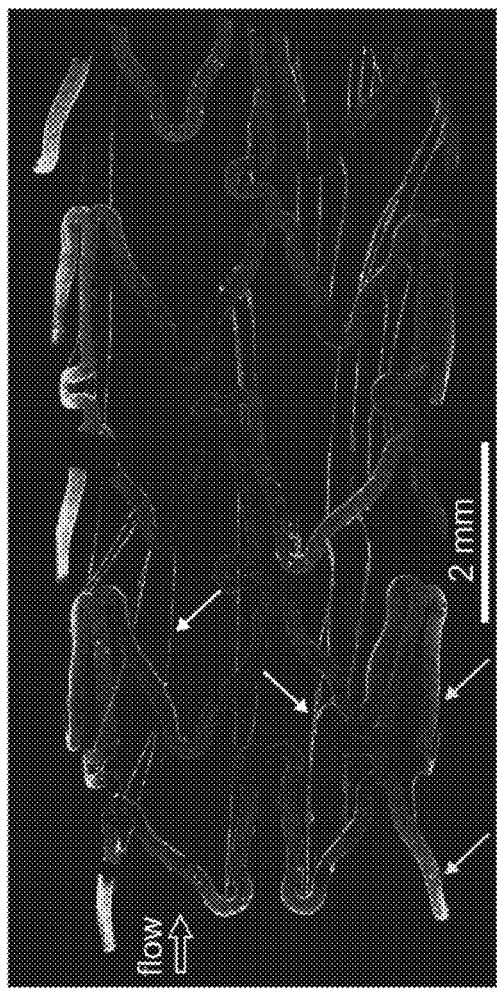
Figure 5B:
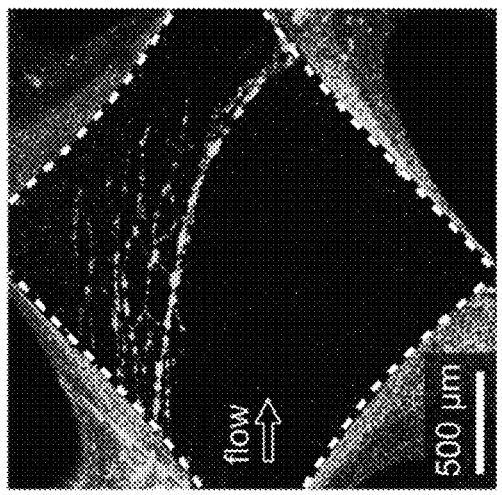

Other systems that suffer from biofilm-induced clogging are spiral-wound reverse osmosis filters (48, 49), which are used, e.g., to purify drinking water. Feed spacer mesh, the element within these filtration devices that is prone to biofilm formation, also displays biofilm streamers that form a network (FIG. 5B). Finally, prosthetic devices can host biofilms that cause chronic infections and other symptoms (1, 2). In particular, biliary stents regularly clog due to slime made up of cholesterol and multispecies biofilms that include *P. aeruginosa* (50). We found that biofilm streamers develop on bare-metal stents within 12 h after inoculation, and span the gaps in the wire mesh (FIG. 5C).

REFERENCES

1. Donlan R M, Costerton J W (2002) Biofilms: Survival mechanisms of clinically relevant microorganisms. Clin Microbiol Rev 15(2):167-193.
2. Hall-Stoodley L, et al. (2012) Towards diagnostic guidelines for biofilm-associated infections. FEMS Immunol Med Microbiol 65(2):127-145.
3. Kolter R, Greenberg E P (2006) Microbial sciences: The superficial life of microbes. Nature 441(7091):300-302.
4. Branda S, Vik S, Friedman L, Kolter R (2005) Biofilms: The matrix revisited. Trends Microbiol 13(1):20-26.
5. Flemming H-C, Wingender J (2010) The biofilm matrix. Nat Rev Microbiol 8(9): 623-633.
6. Escudié R, Cresson R, Delgenès J P, Bernet N (2011) Control of start-up and operation of anaerobic biofilm reactors: A overview of 15 years of research. Water Res 45(1):1-10.
7. Mah T F, et al. (2003) A genetic basis for *Pseudomonas aeruginosa* biofilm antibiotic resistance. Nature 426 (6964):306-310.
8. Nguyen D, et al. (2011) Active starvation responses mediate antibiotic tolerance in biofilms and nutrient-limited bacteria. Science 334(6058):982-986.
9. Whiteley M, et al. (2001) Gene expression in *Pseudomonas aeruginosa* biofilms. Nature 413(6858):860-864.
10. Folsom J P, et al. (2010) Physiology of *Pseudomonas aeruginosa* in biofilms as revealed by transcriptome analysis. BMC Microbiol 10:294.
11. Döotsch A, et al. (2012) The *Pseudomonas aeruginosa* transcriptome in planktonic cultures and static biofilms using RNA sequencing. PLoS ONE 7(2):e31092.
12. Teal T K, Lies D P, Wold B J, Newman D K (2006) Spatiometabolic stratification of *Shewanella oneidensis* biofilms. Appl Environ Microbiol 72(11):7324-7330.
13. Rani S A, et al. (2007) Spatial patterns of DNA replication, protein synthesis, and oxygen concentration within bacterial biofilms reveal diverse physiological states. J Bacteriol 189(11):4223-4233.

14. Nadell C D, Foster K R, Xavier J B (2010) Emergence of spatial structure in cell groups and the evolution of cooperation. PLOS Comput Biol 6(3):e1000716.
15. Picioreanu C, van Loosdrecht M C M, Heijnen J (1998) Mathematical modeling of biofilm structure with a hybrid differential-discrete cellular automaton approach. Biotechnol Bioeng 58(1):101-116.
16. Botzenhardt K, Doring G (1993) Ecology and epidemiology of *Pseudomonas aeruginosa*. *Pseudomonas Aeruginosa* as an Opportunistic Pathogen, eds Campa M, Bendinelli M, Friedman H (Springer, New York), pp 1-7.
17. Sternberg C, Tolker-Nielsen T (2006) Growing and analyzing biofilms in flow cells. Curr Protocols Molec Biol, 10.1002/9780471729259.
18. Busscher H J, van der Mei H C (2006) Microbial adhesion in flow displacement systems. Clin Microbiol Rev 19(1):127-141.
19. Parsek M R, Tolker-Nielsen T (2008) Pattern formation in *Pseudomonas aeruginosa* biofilms. Curr Opin Microbiol 11(6):560-566.
20. Harmsen M, Yang L A, Pamp S J, Tolker-Nielsen T (2010) An update on *Pseudomonas aeruginosa* biofilm formation, tolerance, and dispersal. FEMS Immunol Med Microbiol 59(3):253-268.
21. O'Toole G A, Kolter R (1998) Flagellar and twitching motility are necessary for *Pseudomonas aeruginosa* biofilm development. Mol Microbiol 30(2):295-304.
22. Sauer K, Camper A K, Ehrlich G D, Costerton J W, Davies D G (2002) *Pseudomonas aeruginosa* displays multiple phenotypes during development as a biofilm. J Bacteriol 184(4):1140-1154.
23. Davies D G, et al. (1998) The involvement of cell-to-cell signals in the development of a bacterial biofilm. Science 280(5361):295-298.
24. Friedman L, Kolter R (2004) Genes involved in matrix formation in *Pseudomonas aeruginosa* PA14 biofilms. Mol Microbiol 51(3):675-690.
25. Rusconi R, Lecuyer S, Guglielmini L, Stone H A (2010) Laminar flow around corners triggers the formation of biofilm streamers. J R Soc Interface 7(50):1293-1299.
26. Thullner M (2010) Comparison of bioclogging effects in saturated porous media within one- and two-dimensional flow systems. Ecol Eng 36(2):176-196.
27. Pintelon T R, Picioreanu C, Loosdrecht M C, Johns M L (2012) The effect of biofilm permeability on bioclogging of porous media. Biotechnol Bioeng 109(4): 1031-1042.
28. Rusconi R, Lecuyer S, Autrusson N, Guglielmini L, Stone H A (2011) Secondary flow as a mechanism for the formation of biofilm streamers. Biophys J 100(6):1392-1399.
29. Stoodley P, Lewandowski Z, Boyle J D, Lappin-Scott H M (1998) Oscillation characteristics of biofilm streamers in turbulent flowing water as related to drag and pressure drop. Biotechnol Bioeng 57(5):536-544.
30. Stewart P S (2012) Mini-review: Convection around biofilms. Biofouling 28(2):187-198.
31. Thullner M, Baveye P (2008) Computational pore network modeling of the influence of biofilm permeability on bioclogging in porous media. Biotechnol Bioeng 99(6): 1337-1351.
32. Dupin H J, McCarty P L (2001) Pore-scale modeling of biological clogging due to aggregate expansion: A material mechanics approach. Water Resour Res 37(12): 2965-2979.
33. Stewart T L, Kim D S (2004) Modeling of biomass-plug development and propagation in porous media. Biochem Eng J 17(2):107-119.
34. Williams P, Cámara M (2009) Quorum sensing and environmental adaptation in *Pseudomonas aeruginosa:* A tale of regulatory networks and multifunctional signal molecules. Curr Opin Microbiol 12(2):182-191.
35. Ng W L, Bassler B L (2009) Bacterial quorum-sensing network architectures. Annu Rev Genet 43:197-222.
36. Drescher K, Dunkel J, Cisneros L H, Ganguly S, Goldstein R E (2011) Fluid dynamics and noise in bacterial cell-cell and cell-surface scattering. Proc Natl Acad Sci USA 108(27): 10940-10945.
37. Toutain C M, Caizza N C, Zegans M E, O'Toole G A (2007) Roles for flagellar stators in biofilm formation by *Pseudomonas aeruginosa*. Res Microbiol 158(5):471-477.
38. Klausen M, Aaes-Jørgensen A, Molin S, Tolker-Nielsen T (2003) Involvement of bacterial migration in the development of complex multicellular structures in *Pseudomonas aeruginosa* biofilms. Mol Microbiol 50(1):61-68.
39. Barken K B, et al. (2008) Roles of type IV pili, flagellum-mediated motility and extracellular DNA in the formation of mature multicellular structures in *Pseudomonas aeruginosa* biofilms. Environ Microbiol 10(9):2331-2343.
40. Sakuragi Y, Kolter R (2007) Quorum-sensing regulation of the biofilm matrix genes (pel) of *Pseudomonas aeruginosa*. J Bacteriol 189(14):5383-5386.
41. Fierer N, Bradford M A, Jackson R B (2007) Toward an ecological classification of soil bacteria. Ecology 88(6): 1354-1364.
42. Brown D G, Stencel J R, Jaffé P R (2002) Effects of porous media preparation on bacteria transport through laboratory columns. Water Res 36(1):105-114.
43. Stoodley P, Dodds I, De Beer D, Scott H L, Boyle J D (2005) Flowing biofilms as a transport mechanism for biomass through porous media under laminar and turbulent conditions in a laboratory reactor system. Biofouling 21(3-4):161-168.
44. Zhang C, et al. (2010) Effects of pore-scale heterogeneity and transverse mixing on bacterial growth in porous media. Environ Sci Technol 44(8):3085-3092.
45. Kim J W, Choi H, Pachepsky Y A (2010) Biofilm morphology as related to the porous media clogging. Water Res 44(4):1193-1201.
46. Kapellos G E, Alexiou T S, Payatakes A C (2007) Hierarchical simulator of biofilm growth and dynamics in granular porous materials. Adv Water Resour 30(6-7): 1648-1667.
47. Leis A P, Schlicher S, Franke H, Strathmann M (2005) Optically transparent porous medium for nondestructive studies of microbial biofilm architecture and transport dynamics. Appl Environ Microbiol 71(8):4801-4808.
48. Vrouwenvelder J S, Graf von der Schulenburg D A, Kruithof J C, Johns M L, van Loosdrecht M C M (2009) Biofouling of spiral-wound nanofiltration and reverse osmosis membranes: A feed spacer problem. Water Res 43(3):583-594.
49. Marty A, Rogues C, Causserand C, Bacchin P (2012) Formation of bacterial streamers during filtration in microfluidic systems. Biofouling 28(6):551-562.
50. Guaglianone E, et al. (2010) Microbial biofilms associated with biliary stent clogging. FEMS Immunol Med Microbiol 59(3):410-420.

51. Lanzer M, Bujard H (1988) Promoters largely determine the efficiency of repressor action. Proc Natl Acad Sci USA 85(23):8973-8977.
52. Lambertsen L, Sternberg C, Molin S (2004) Mini-Tn7 transposons for site-specific tagging of bacteria with fluorescent proteins. Environ Microbiol 6(7):726-732.
53. Choi K H, et al. (2005) A Tn7-based broad-range bacterial cloning and expression system. Nat Methods 2(6):443-448.
54. Unger M A, Chou H P, Thorsen T, Scherer A, Quake S R (2000) Monolithic microfabricated valves and pumps by multilayer soft lithography. Science 288(5463): 113-116.
55. Chen M Y, Lee D J, Tay J H (2007) Distribution of extracellular polymeric substances in aerobic granules. Appl Microbiol Biotechnol 73(6):1463-1469.
56. Strathmann M, Wingender J, Flemming H C (2002) Application of fluorescently labelled lectins for the visualization and biochemical characterization of polysaccharides in biofilms of *Pseudomonas aeruginosa*. J Microbiol Methods 50(3):237-248.
57. Whitchurch C B, Tolker-Nielsen T, Ragas P C, Mattick J S (2002) Extracellular DNA required for bacterial biofilm formation. Science 295(5559):1487-1487.

What is claimed is:

1. A system for measuring biofilm streamers comprising:
   a. at least one channel, wherein the channel comprises an inlet, an outlet, a lumen, and at least one biofilm streamer promotion element, wherein a fluid moves through the lumen in a flow driven by a controlled pressure;
   b measuring element capable of measuring a flow rate of the fluid through the channel, wherein the measuring element:
      (i) receives the fluid in an effluent collecting element after the fluid moves through the lumen;
      (ii) measures the weight of the received fluid as a function of time using an analytical balance; and
      (iii) communicates the measured weight to a computer, wherein the computer determines the change in weight of the received fluid as a function of time.

2. The system of claim 1, wherein the controlled pressure is provided by a pumping element or gravity.

3. The system of claim 2, wherein the pumping element is a syringe, a weight, or a pump.

4. The system of claim 1, wherein the biofilm streamer comprises bacterium capable of producing a biofilm streamer.

5. The system of claim 1, wherein the effluent collecting element is a dish.

6. The system of claim 2, wherein the pumping element is a reservoir suspended above the height of the effluent collecting element, wherein a height differential between the reservoir and the effluent collecting element determines the controlled pressure applied to the fluid.

7. The system of claim 1 further comprising a substrate.

8. The system of claim 7, wherein the substrate is a glass coverslip.

9. The system of claim 1, further comprising a microscope capable of imaging the channel.

10. The system of claim 9, wherein the microscope is capable of imaging biofilm streamer growth.

11. The system of claim 9, wherein the microscope is capable of imaging biofilm streamer morphology.

12. The system of claim 9, wherein the microscope is a confocal laser scanning microscope or an epifluorescence microscope.

13. The system of claim 1, wherein the biofilm streamer promotion element is selected from: a curved channel, a channel with at least one turn, a channel with at least one corner, an edge projecting into the lumen of the channel, a mound projecting into the lumen of the channel, a channel with roughened surfaces, and one or more objects placed within the channel lumen.

14. The system of claim 1, wherein the channel has at least 2, 3, 4, 5, 6, 7, 8, 9, 10 or 36 corners.

15. The system of claim 1, wherein the channel has 1 turn about every 400 um.

16. The system of claim 1, wherein the flow of the fluid is laminar flow.

17. The system of claim 1, wherein the flow of the fluid is turbulent flow.

18. The system of claim 1, wherein the flow is characterized by a Reynolds number of less than 2000.

19. The system of claim 1, wherein the flow is characterized by a Reynolds number of greater than 2000.

20. The system of claim 1, wherein the flow rate comprises a shear stress of between 0.01 and 100 Pa.

21. The system of claim 1, wherein the biofilm streamer promotion element is amorphous particles of fluoropolymer placed within the channel lumen.

22. The system of claim 1, wherein the biofilm streamer promotion element is a channel comprising welded polypropylene feed spacer mesh.

23. The system of claim 1, wherein the channel is circular.

24. The system of claim 1, wherein the system further comprises a three-inlet port capable of being opened and closed.

25. The system of claim 24, wherein the three-inlet port further comprises multilayer microfluidic gates.

26. The system of claim 1, wherein the channel is selected from: a stent, a pipe, or a cooling tower.

27. The system of claim 1, wherein the computer continually samples the weight of the received fluid in the effluent collecting element as a function of time and converts the weight of the received fluid to a flow rate.

28. The system of claim 1, wherein the computer periodically samples the weight of the received fluid in the effluent collecting element as a function of time and converts the weight of the received fluid to a flow rate.

29. The system of claim 1, wherein the flow rate comprises a shear stress of between 0.01 and 10 Pa.

30. A method of measuring a biofilm streamer comprising:
   a. passing a fluid through the system of claim 1;
   b. monitoring the flow rate over time; and
   c. determining either the time until clogging (T) or the duration of the clogging transition ($\tau$).

31. The method of claim 30, wherein the method further comprises imaging the growth of the biofilm streamer over time.

32. The method of claim 30, wherein the method further comprises imaging the morphology of the biofilm streamer over time.

33. The method of claim 30, wherein the method further comprises:
   a. adding a test compound to the fluid; and
   b. comparing the time until clogging (T) or the duration of the clogging transition ($\tau$) in the presence and in the absence of said test compound.

34. The method of claim 30, wherein the method further comprises:
- a. adding a test compound to the fluid; and
- b. comparing the growth or morphology of the biofilm streamer in the presence and in the absence of said test compound.

* * * * *